US012754188B2

(12) United States Patent
Grothe et al.

(10) Patent No.: US 12,754,188 B2
(45) Date of Patent: Oct. 6, 2026

(54) ANALYTE CHARACTERIZATION VIA ITERATIVE ANALYSIS

(71) Applicant: Nautilus Subsidiary, Inc., Seattle, WA (US)

(72) Inventors: Robert Grothe, San Jose, CA (US); James Henry Joly, San Francisco, CA (US); Giovanni Bellesia, Santa Clara, CA (US); Michael Flaster, Menlo Park, CA (US); Jarrett D. Egertson, Rancho Palos Verdes, CA (US)

(73) Assignee: NAUTILUS SUBSIDIARY, INC., Seattle, WA (US)

( * ) Notice: Subject to any disclaimer, the term of this patent is extended or adjusted under 35 U.S.C. 154(b) by 0 days.

(21) Appl. No.: 19/390,106

(22) Filed: Nov. 14, 2025

(65) Prior Publication Data

US 2026/0110692 A1 Apr. 23, 2026

Related U.S. Application Data

(63) Continuation of application No. 19/342,315, filed on Sep. 26, 2025.

(60) Provisional application No. 63/761,498, filed on Feb. 21, 2025, provisional application No. 63/708,670, filed on Oct. 17, 2024.

(51) Int. Cl.

| | |
|---|---|
| ***G01N 33/68*** | (2006.01) |
| ***G16B 15/30*** | (2019.01) |
| ***G16B 35/00*** | (2019.01) |
| ***G16B 40/20*** | (2019.01) |

(52) U.S. Cl.

CPC ......... *G01N 33/6845* (2013.01); *G16B 15/30* (2019.02); *G16B 35/00* (2019.02); *G16B 40/20* (2019.02)

(58) Field of Classification Search

None

See application file for complete search history.

(56) References Cited

U.S. PATENT DOCUMENTS

| | | | |
|---|---|---|---|
| 2023/0360732 | A1 | 11/2023 | Egertson et al. |
| 2026/0110691 | A1 | 4/2026 | Grothe et al. |

FOREIGN PATENT DOCUMENTS

| | | | |
|---|---|---|---|
| WO | WO 2019/133892 | 7/2019 | |
| WO | WO-2023064181 A1 * | 4/2023 | ............. G16B 35/10 |
| WO | WO 2026/084863 | 4/2026 | |

* cited by examiner

*Primary Examiner* — Kaijiang Zhang

(74) *Attorney, Agent, or Firm* — Knobbe, Martens, Olson & Bear LLP

(57) ABSTRACT

Methods, reagents, kits and systems for characterizing different proteins of interest are provided. The provided methods, systems, etc. provide detection, characterization of proteins for different biologically relevant proteins for monitoring and characterizing biological processes.

14 Claims, 9 Drawing Sheets

Without Adaptive Decode

| Sample | Measured Protein: G6PI | Measured Protein: Transferrin | Measured Protein: Model Protein |
|---|---|---|---|
| G6PI | 0.88 | 0.09 | 0.04 |
| Transferrin | 0.10 | 0.88 | 0.02 |
| Model Protein | 0.10 | 0.01 | 0.89 |

With Adaptive Decode

| Sample | Measured Protein: G6PI | Measured Protein: Transferrin | Measured Protein: Model Protein |
|---|---|---|---|
| G6PI | 1.00 | 0.00 | 0.00 |
| Transferrin | 0.00 | 1.00 | 0.00 |
| Model Protein | 0.00 | 0.00 | 1.00 |

Figure 9

ANALYTE CHARACTERIZATION VIA ITERATIVE ANALYSIS

CROSS-REFERENCE TO RELATED APPLICATIONS

This application is a continuation of U.S. application Ser. No. 19/342,315 filed Sep. 26, 2025, which claims priority to U.S. Prov. App. 63/708,670, filed Oct. 17, 2024, entitled "ANALYTE CHARACTERIZATION VIA ITERATIVE ANALYSIS"; and U.S. Prov. App. 63/761,498, filed Feb. 21, 2025, entitled "ANALYTE CHARACTERIZATION VIA ITERATIVE ANALYSIS", which are each incorporated by reference in its entirety.

FIELD OF THE INVENTION

Embodiments relate to techniques for characterizing proteins using a comparatively small number of affinity reagents that are not highly specific for an individual protein. The affinity reagents may be capable of binding to larger subsets of the proteins of a proteome to characterize proteins.

BACKGROUND

Biological researchers are constantly seeking better ways to investigate the functions of living things, to understand the keys to life and health, the causes of disease and dysfunction, and to help identify possible paths of intervention or influence to achieve better outcomes for all of these.

High throughput, highly sensitive detection and analysis technologies have given rise to great advances in the field of biological research. For example, medical research and clinical diagnostics have seen significant advances resulting from the emergence of high throughput technology platforms that routinely decode the human genome or human transcriptome in a matter of hours. An individual's genome, as a blueprint for the components of a given biological system, can provide some insights into development, behavior, risk of disease, responsiveness to therapeutic treatments, longevity and many other characteristics. As such, the genome can provide a powerful source for evaluating risk and predicting outcomes to certain treatments or medications.

Likewise, an individual's transcriptome is the collection of RNA transcripts that are expressed from the genome. The RNA transcripts are, in turn, translated into proteins which may, in some cases be further modified post translationally. The proteins function as the workhorses that perform the biological functions in biological systems, as instructed by the genome. In some cases, characterization and quantification of the transcriptome can lead to clinically relevant diagnoses or prognoses for a given biological system, e.g., a patient.

The advent of high-throughput, relatively inexpensive and routine genetic analysis tools and processes has made genomic or transcriptomic analysis a convenient starting point in looking at biological functions. Unfortunately, however, these analyses are really directed at proxies for actual biological function. The genome, for example, is a snapshot of a blueprint, in many cases, taken at conception, that provides very little insight into the present functioning of a biological system. The transcriptome, on the other hand, provides a more contemporaneous measure of that biological function, but still falls short of actual biological operations beyond a measure of what genes are transcribed when.

The information provided, again, is removed from the actual biological functions being carried out at any given moment in time within the biological system, and as a result, in many cases, provides inadequate diagnostic or prognostic precision to guide treatment.

To gain more insightful views into the function, dysfunction, and manipulation of biological systems, researchers need analytical systems and methods that measure the actual biological operations that are occurring within these biological systems, including looking at the presence, prevalence, flux, and function of the various proteins within those systems. The set of proteins present within a given biological system is generally referred to as the proteome of that system.

Characterizing the various proteins in a biological system at any given time potentially yields significant amounts of information as to the functioning of that system. Accordingly, it is highly desirable to provide methods, systems and reagents for use in being able to accurately and sensitively characterize a variety of different proteins within the proteomes of biological systems. Unfortunately, many existing technologies for analyzing proteins, such as protein or peptide sequencing technologies, mass spectrometry methods, and the like, lack the ability to both comprehensively characterize proteins at high throughput and high sensitivity.

SUMMARY

One of the innovative aspects of this disclosure includes a method including depositing proteins from a sample onto a substrate, each of the proteins attached to unique spatial addresses on the substrate; carrying out a series of affinity binding measurements by exposing the proteins attached to the unique spatial addresses on the substrate to a series of affinity reagents, thereby producing an observed binding measurements model indicating positive binding measurement outcomes and negative binding measurement outcomes for the proteins with the affinity reagents; receiving a first probe probability binding model indicating probabilities of the positive binding measurement outcomes and the negative binding measurement outcomes for the proteins exposed to the affinity reagents; receiving first abundance information of the proteins of the sample; and determining in an iterative process, starting with (i) the observed binding measurements model, (ii) the first probe probability binding model, and (iii) the first abundance information, an updated abundance information of the proteins deposited onto the substrate and an updated probe probability binding model.

In some implementations, the iterative process includes an application of an Expectation-Maximization method, wherein latent variables include identification information of proteins, and model parameters include the updated abundance information and the updated probe probability binding model.

In some implementations, the first abundance information indicates a uniform distribution of proteins for candidate proteins within the sample or proteins on the substrate.

In some implementations, the updated abundance information of the proteins deposited onto the substrate is based on pseudocounts representing probabilistic identities of the proteins.

In some implementations, the pseudocounts include partitioning a unitary value of a protein among candidate proteins.

In some implementations, a quantitation of a candidate protein in the sample includes summing the pseudocounts assigned to the candidate protein.

In some implementations, partitioning is based on probabilities of the protein for each of the candidate proteins.

In some implementations, the method includes providing the updated abundance information in a second iteration as abundances of the proteins in the sample, thereby quantifying the proteins.

In some implementations, the first abundance information indicates a non-uniform distribution of proteins for candidate proteins within the sample or proteins on the substrate.

In some implementations, the first abundance information is based on reference values based on an origin or type of the sample.

In some implementations, some of the probabilities indicated in the first probe probability binding model are based on observed binding measurements of single recombinant proteins in a first lane of a flow cell, the flow cell also having a second lane where the sample is deposited thereon.

In some implementations, some of the probabilities indicated in the first probe probability binding model are based on single recombinant proteins used in previous experiments.

In some implementations, the updated abundance information is restrained based on a prior distribution based on a mean and a variance for the abundance of each of the candidate proteins.

In some implementations, the updated probe probability binding model is restrained based on a prior distribution for the probabilities of the positive binding measurement outcomes and the negative binding measurement outcomes for the proteins exposed to the affinity reagents.

In some implementations, determining, in the iterative process, the updated abundance information and the updated probe probability model includes determining protein identification information based on the observed binding measurements model, the first probe probability binding model, and the first abundance information.

In some implementations, the updated abundance information and the updated probe probability model are based on the protein identification information.

Another innovative aspect of the disclosure includes system having a substrate having proteins deposited thereon, each of the proteins attached to unique spatial addresses on the substrate; a fluidic system configured to carry out a series of affinity binding measurements by exposing the proteins attached to the unique spatial addresses on the substrate to a series of affinity reagents; a detector configured to monitor the series of affinity binding measurements and thereby produce an observed binding measurements model indicating positive binding measurement outcomes and negative binding measurement outcomes for the proteins with the affinity reagents; and a computing device configured to: receive a first probe probability binding model indicating probabilities of the positive binding measurement outcomes and the negative binding measurement outcomes for the proteins exposed to the affinity reagents; receive first abundance information of the proteins of the sample, determine in an iterative process, starting with (i) the observed binding measurements model, (ii) the first probe probability binding model, and (iii) the first abundance information, an updated abundance information of the proteins deposited onto the substrate and an updated probe probability binding model.

In some implementations, the computing device is further configured to perform any of the methods or techniques described in this section.

Another innovative aspect of the disclosure includes a computer program product, comprising one or more non-transitory computer-readable media having computer program instructions stored therein, the computer program instructions being configured such that, when executed by one or more computing devices, the computer program instructions cause the one or more computing devices to: receive an observed binding measurements model indicating positive binding measurements outcomes and negative binding measurement outcomes from exposing proteins attached to unique spatial addresses on a substrate to a series of affinity reagents; receive a first probe probability binding model indicating probabilities of the positive binding measurement outcomes and the negative binding measurement outcomes for the proteins exposed to the series of affinity reagents; receive first abundance information of the proteins of the sample; and determine in an iterative process, starting with (i) the observed binding measurements model, (ii) the first probe probability binding model, and (iii) the first abundance information, an updated abundance information of the proteins deposited onto the substrate and an updated probe probability binding model.

In some implementations, the computer program instructions cause the one or more computing devices to perform any of the methods or techniques described in this section.

Another innovative aspect of this disclosure includes a method including receiving a list of M candidate proteins that might be present in a biological sample; receiving an initial estimate of protein abundances of each of the M candidate proteins present in the biological sample; receiving a list of N probes that will be used to identify the proteins in the biological sample; receiving an initial estimate of an M×N probe-to-protein binding model matrix, where each entry of the matrix indicates a probability of measuring a binding event between a protein from the list of candidate proteins and a probe from the list of probes used to identify the proteins; depositing single protein molecules from the sample onto a substrate, wherein each of Q unique spatial addresses on the substrate has a single protein molecule attached; carrying out N cycles of binding measurements by exposing the proteins attached to the Q unique spatial addresses on the substrate to the N probes, wherein each cycle exposes the proteins to one of the N probes, to obtain a Q×N binding measurement matrix where each entry of the matrix indicates whether or not a binding event was observed at each spatial address in each cycle; and determining by using an iterative process, starting with (i) the binding measurement matrix, (ii) the initial estimate of the protein abundance vector, and (iii) the initial estimate of the probe-to-protein binding model matrix, a final estimate of the protein abundances and a final estimate of the probe-to-protein binding model matrix.

Another innovative aspect of this disclosure includes depositing proteins from a sample onto a substrate, each of the proteins attached to unique spatial addresses on the substrate; carrying out a series of affinity binding measurements by exposing the proteins attached to the unique spatial addresses on the substrate to a series of affinity reagents, thereby producing an observed binding measurements model indicating positive binding measurement outcomes and negative binding measurement outcomes for the proteins with the affinity reagents; receiving a first probe probability binding model indicating probabilities of the positive binding measurement outcomes and the negative binding measurement outcomes for the proteins exposed to the affinity reagents; receiving initial abundance information of the proteins of the sample, the initial abundance information representing an estimate of quantities of proteins of the sample; and characterizing the proteins deposited onto the substrate by performing an iterative process of determining protein identification information based on (i) the observed binding measurements model, (ii) the first probe probability binding model, and (iii) the initial abundance information.

In some implementations, characterizing the proteins includes identifying proteoforms of the proteins.

In some implementations, characterizing the proteins includes quantifying proteoforms of the proteins.

In some implementations, characterizing the proteins includes updating the first probe probability binding model based on the protein identification information.

In some implementations, characterizing the proteins includes updating the initial abundance information based on the protein identification information.

Another innovative aspect of this disclosure is a method including depositing proteins from a sample onto a substrate, each of the proteins attached to unique spatial addresses on the substrate; carrying out a series of affinity binding measurements by exposing the proteins attached to the unique spatial addresses on the substrate to a series of affinity reagents, thereby producing an observed binding measurements model indicating positive binding measurement outcomes and negative binding measurement outcomes for the proteins with the affinity reagents; receiving a first probe probability binding model indicating probabilities of the positive binding measurement outcomes and the negative binding measurement outcomes for proteoforms of the proteins exposed to the affinity reagents; receiving first abundance information of the proteoforms of the proteins of the sample; and determining in an iterative process, starting with (i) the observed binding measurements model, (ii) the first probe probability binding model, and (iii) the first abundance information, an updated abundance information of the proteoforms of the proteins deposited onto the substrate and an updated probe probability binding model.

In some implementations, the proteins are Tau proteins.

In some implementations, the candidate proteins are proteoforms of the proteins.

Another innovative aspect of the disclosure is a system including a substrate having proteins deposited thereon, each of the proteins attached to unique spatial addresses on the substrate; a fluidic system configured to carry out a series of affinity binding measurements by exposing the proteins attached to the unique spatial addresses on the substrate to a series of affinity reagents; a detector configured to monitor the series of affinity binding measurements and thereby produce an observed binding measurements model indicating positive binding measurement outcomes and negative binding measurement outcomes for the proteins with the affinity reagents; and a computing device configured to: receive a first probe probability binding model indicating probabilities of the positive binding measurement outcomes and the negative binding measurement outcomes for proteoforms of the proteins exposed to the affinity reagents; receive first abundance information of the proteoforms of the proteins of the sample, determine in an iterative process, starting with (i) the observed binding measurements model, (ii) the first probe probability binding model, and (iii) the first abundance information, an updated abundance information of the proteoforms of the proteins deposited onto the substrate and an updated probe probability binding model for the proteoforms of the proteins.

In some implementations, the proteins are Tau proteins.

Another innovative aspect of the disclosure includes a method for characterizing proteins, including depositing proteins from a sample onto a substrate, each of the proteins attached to unique spatial addresses on the substrate; carrying out a series of affinity binding measurements by exposing the proteins attached to the unique spatial addresses on the substrate to a series of affinity reagents, thereby producing an observed binding measurements model indicating positive binding measurement outcomes and negative binding measurement outcomes for the proteins with the affinity reagents; receiving a first probe probability binding model indicating estimated probabilities of the affinity reagents binding to candidate proteins that may be in the sample; receiving first abundance information of the proteins of the sample; and determining in an iterative process, starting with (i) the observed binding measurements model, (ii) the first probe probability binding model, and (iii) the first abundance information, a first updated abundance information of the proteins deposited onto the substrate and a first updated probe probability binding model.

In some implementations, the first abundance information indicates a uniform distribution of proteins for candidate proteins within the sample or proteins on the substrate.

In some implementations, the first abundance information indicates a uniform distribution of post-translational modifications (PTMs) for candidate proteoforms of the proteins within the sample or proteins on the substrate.

In some implementations, the proteins are of a same protein species, and the first updated abundance information of the proteins includes abundance information of proteoforms of the same protein species.

In some implementations, the method includes determining a data likelihood that the observed binding measurements model would be produced by the candidate proteins indicated in the probe probability binding model; and generating probabilities of each of the proteins being each of the candidate proteins based on the data likelihood and the initial abundance information, wherein the first updated abundance information and the first updated probe probability binding model is based on the probabilities of each of the proteins being each of the candidate proteins.

In some implementations, the method includes determining, in a second iteration of the iterative process, second updated abundance information of the proteins in the sample based on the first updated abundance information and the first updated probe probability binding model, thereby quantifying the proteins.

In some implementations, the second iteration includes determining a second probe probability binding model based on the first updated abundance information and the second probe probability binding model.

Another innovative aspect of the disclosure includes a method for characterizing proteins, including depositing proteins from a sample onto a substrate, each of the proteins attached to unique spatial addresses on the substrate; carrying out a series of affinity binding measurements by exposing the proteins attached to the unique spatial addresses on the substrate to a series of affinity reagents, thereby producing an observed binding measurements model indicating positive binding measurement outcomes and negative binding measurement outcomes for the proteins with the affinity reagents; receiving a first probe probability binding model indicating estimated probabilities of the affinity reagents binding to candidate proteins that may be in the sample; receiving first abundance information of the proteins of the sample; and determining in an iterative process, starting with (i) the observed binding measurements model, (ii) the first probe probability binding model, and (iii) the first abundance information, a first updated abundance information of the proteins deposited onto the substrate and a first updated probe probability binding model.

In some implementations, the first abundance information indicates a uniform distribution of proteins for candidate proteins within the sample or proteins on the substrate.

In some implementations, the first abundance information indicates a uniform distribution of post-translational modifications (PTMs) for candidate proteoforms of the proteins within the sample or proteins on the substrate.

In some implementations, the proteins are of a same protein species, and the first updated abundance information of the proteins includes abundance information of proteoforms of the same protein species.

In some implementations, the method includes determining a data likelihood that the observed binding measurements model would be produced by the candidate proteins indicated in the probe probability binding model; and generating probabilities of each of the proteins being each of the candidate proteins based on the data likelihood and the initial abundance information, wherein the first updated abundance information and the first updated probe probability binding model is based on the probabilities of each of the proteins being each of the candidate proteins.

In some implementations, the method includes determining, in a second iteration of the iterative process, second updated abundance information of the proteins in the sample based on the first updated abundance information and the first updated probe probability binding model, thereby quantifying the proteins.

In some implementations, the second iteration includes determining a second probe probability binding model based on the first updated abundance information and the second probe probability binding model.

Another innovative aspect of the disclosure includes a system for characterizing proteins, including a substrate having proteins deposited thereon, each of the proteins attached to unique spatial addresses on the substrate; a fluidic system configured to carry out a series of affinity binding measurements by exposing the proteins attached to the unique spatial addresses on the substrate to a series of affinity reagents; a detector configured to monitor the series of affinity binding measurements and thereby produce an observed binding measurements model indicating positive binding measurement outcomes and negative binding measurement outcomes for the proteins with the affinity reagents; and a computing device configured to: receive a first probe probability binding model indicating estimated probabilities of the affinity reagents binding to candidate proteins that may be in the sample; receive first abundance information of the proteins of the sample; and determine in an iterative process, starting with (i) the observed binding measurements model, (ii) the first probe probability binding model, and (iii) the first abundance information, a first updated abundance information of the proteins deposited onto the substrate and a first updated probe probability binding model.

In some implementations, the first abundance information indicates a uniform distribution of proteins for candidate proteins within the sample or proteins on the substrate.

In some implementations, the first abundance information indicates a uniform distribution of post-translational modifications (PTMs) for candidate proteoforms of the proteins within the sample or proteins on the substrate.

In some implementations, the proteins are of a same protein species, and the first updated abundance information of the proteins includes abundance information of proteoforms of the same protein species.

In some implementations, computing device is configured to determine a data likelihood that the observed binding measurements model would be produced by the candidate proteins indicated in the probe probability binding model; and generate probabilities of each of the proteins being each of the candidate proteins based on the data likelihood and the initial abundance information, wherein the first updated abundance information and the first updated probe probability binding model is based on the probabilities of each of the proteins being each of the candidate proteins.

In some implementations, the computing device is configured to determine, in a second iteration of the iterative process, second updated abundance information of the proteins in the sample based on the first updated abundance information and the first updated probe probability binding model, thereby quantifying the proteins.

In some implementations, the second iteration includes determining a second probe probability binding model based on the first updated abundance information and the second probe probability binding model.

Another innovative aspect of the disclosure includes a computer program product, comprising one or more non-transitory computer-readable media having computer program instructions stored therein, the computer program instructions being configured such that, when executed by one or more computing devices, the computer program instructions cause the one or more computing devices to receive an observed binding measurements model indicating positive binding measurement outcomes and negative binding measurement outcomes for proteins with affinity reagents, the observed binding measurements model based on a series of affinity binding measurements exposing the proteins attached to the unique spatial addresses on a substrate to a series of affinity reagents, thereby producing the observed binding measurements model; receive a first probe probability binding model indicating estimated probabilities of the affinity reagents binding to candidate proteins that may be in the sample; receive first abundance information of the proteins of the sample; and determine in an iterative process, starting with (i) the observed binding measurements model, (ii) the first probe probability binding model, and (iii) the first abundance information, a first updated abundance information of the proteins deposited onto the substrate and a first updated probe probability binding model.

In some implementations, the first abundance information indicates a uniform distribution of proteins for candidate proteins within the sample or proteins on the substrate.

In some implementations, the first abundance information indicates a uniform distribution of post-translational modifications (PTMs) for candidate proteoforms of the proteins within the sample or proteins on the substrate.

In some implementations, the proteins are of a same protein species, and the first updated abundance information of the proteins includes abundance information of proteoforms of the same protein species.

In some implementations, the computer program product includes determining a data likelihood that the observed binding measurements model would be produced by the candidate proteins indicated in the probe probability binding model; and generating probabilities of each of the proteins being each of the candidate proteins based on the data likelihood and the initial abundance information, wherein the first updated abundance information and the first updated probe probability binding model is based on the probabilities of each of the proteins being each of the candidate proteins.

In some implementations, the computer program product includes determining, in a second iteration of the iterative process, second updated abundance information of the proteins in the sample based on the first updated abundance information and the first updated probe probability binding model, thereby quantifying the proteins.

In some implementations, the second iteration includes determining a second probe probability binding model based on the first updated abundance information and the second probe probability binding model.

DESCRIPTION OF THE FIGURES

FIG. 9 shows an example of the results of analyte characterization via an iterative process.

DETAILED DESCRIPTION

Figure 1:
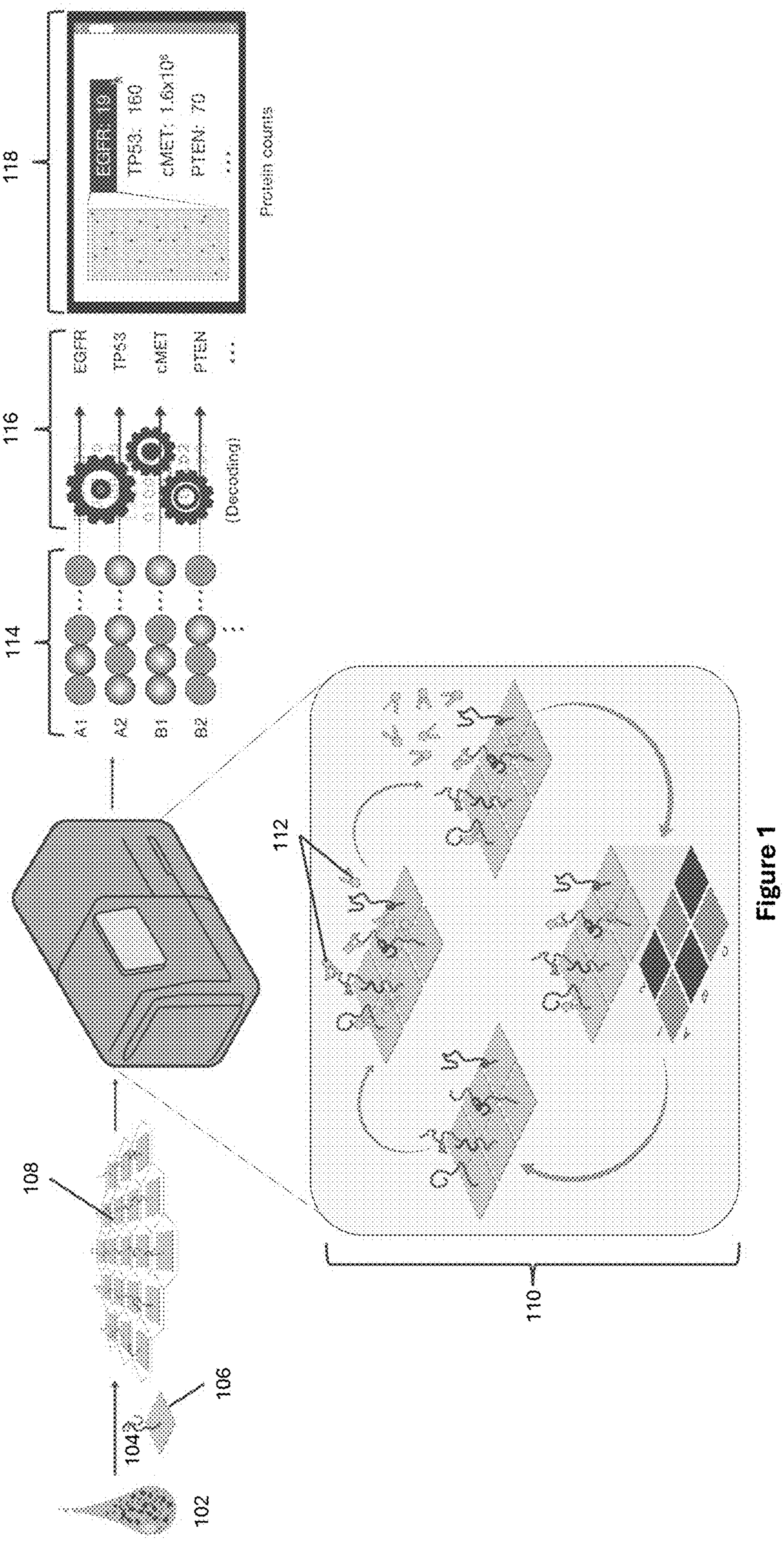
FIG. 1 schematically illustrates an example of a protein analysis process and system.

Some analytes, such as proteins, can be detected using one or more affinity reagents having known or measurable binding affinity for the protein. For example, an affinity reagent can bind a protein to form a complex and a signal produced by the complex is detected. A protein that is detected by binding to a known affinity reagent can be identified based on the known or predicted binding characteristics of the affinity reagent. For example, an affinity reagent that is known to selectively bind a candidate protein suspected of being in a sample, without substantially binding to other proteins in the sample, can be used to identify the candidate protein in the sample merely by detecting the binding event. This one-to-one correlation of affinity reagent to candidate protein can be used for identification of one or more proteins. However, as the protein complexity (i.e., the number and variety of different proteins) in a sample increases, the time and resources to produce a commensurate variety of affinity reagents having one-to-one specificity for the proteins approaches the limits of practicality.

This disclosure describes techniques for characterizing proteins using a comparatively small number of affinity reagents that are not highly specific for an individual protein, but instead are capable of binding larger subsets of the proteins of a proteome. For example, the number of proteins characterized can be at least 5×, 10×, 25×, 50×, 100×, 200×, or more than the number of affinity reagents used. The binding events between these affinity reagents and proteins are detected and, via an iterative "decoding" process, the proteins within the sample are characterized which can include quantifying and/or identifying the proteins. Additionally, the proteins within the sample can be characterized to quantify and/or identify proteoforms, including isoforms and post-translational modifications of proteins.

For example, individual protein molecules from a sample may be immobilized on a solid surface of an array such that each of the immobilized proteins is attached to a unique spatial address of the array. A series of affinity reagents are applied as probes to generate an observed binding measurements model indicating positive and negative binding measurement outcomes for the affinity reagents interacting with the immobilized proteins. Different affinity reagents bind to multiple of the immobilized proteins, but not all the proteins, resulting in a "pattern" of positive and negative binding measurement outcomes that were observed for each of the immobilized proteins on the array.

The observed binding measurements model is used with a probe probability binding model indicating the estimated probabilities of the affinity reagents binding to candidate proteins (i.e., possible proteins that may be among the immobilized proteins or within the sample) and an initial abundance information of the immobilized proteins or the sample (e.g., a uniform distribution of the candidate proteins as an initial starting point) to "decode" the probed immobilized proteins and identify various characteristics of those immobilized proteins. The decoding is done by performing an iterative process to determine identification information related to probabilities of the immobilized proteins identified as the candidate proteins and then use the identification information to determine updated abundance information that might be more accurate than the initial abundance information. As described later herein, the identification information and updated abundance information can be based on "pseudocounts" that are fractional representations of each immobilized protein, though a "winner-takes-all" approach based on the probabilities may also be used. In addition, an updated probe probability binding model is determined using the identification information and observed binding measurements model, resulting in changes to the probabilities for the binding between the affinity reagents and candidate proteins.

Next, in a subsequent iteration, new identification information is determined using the updated abundance information and the updated probe probability model that were previously generated in the first iteration. This results in new determinations of updated abundance information and updated probe probability binding model that are updated again to be adapted to new circumstances—i.e., the newly acquired updated probe probability binding model and the newly acquired updated abundance information from the prior iteration. This iterative process continues until a convergence condition is satisfied, resulting in a final characterization of the proteins which includes a final updated abundance information that more accurately quantifies the immobilized proteins from the sample.

The iterative process allows for a more accurate characterization, including quantification, of the immobilized proteins on the array. This is due to the iterative process compensating for uncertainty in the probe probability binding model. Moreover, the iterative process also compensates for run-to-run variations, for example, manufacturing variations of the instrument and/or array, environmental conditions, and lot differences between affinity reagents. Thus, the techniques described herein provide a more accurate characterization of proteins.

In more detail, analysis of protein abundances begins with the isolation of individual protein or polypeptide molecules in a manner that allows for their individual interrogation and analysis at the single molecule level. In general, individual protein molecules within a sample may be isolated by immobilizing them on a solid support. In some cases, this may include isolation of an individual protein molecule of a sample on a bead or particle that may be individually interrogated and analyzed, while in other cases, individual protein molecules may be immobilized on different locations on a solid surface of an array, such that the different locations hosting the immobilized proteins may be individually interrogated and separately analyzed.

One example of an array-based approach for protein analysis uses the approach described in, e.g., U.S. Pat. Nos. 10,473,654B1, 11,545,234B1, and Eggertson, et al., A theoretical framework for proteome-scale single-molecule protein identification using multi-affinity protein binding reagents, bioRxiv, doi.org/10.1101/2021.10.11.463967, the full disclosures of which are hereby incorporated herein by reference in their entirety for all purposes, where individual protein molecules are coupled to the surface of an array and spaced apart in separate, optically resolvable locations or addresses. The individual proteins are then iteratively probed using detectable affinity reagents that bind to identifiable traits of the proteins, such as specific structural components, e.g., specific amino acid sequences or sequence contexts. These bound affinity reagents may then be detected, indicating the presence of that particular identifiable trait in the protein or polypeptide that is immobilized at that location.

For example, in many of the techniques described herein, affinity reagents used are capable of binding to small subunits of the proteins, like trimers or tetramer epitopes (3 or 4 amino acid segments) or other short or small sequence contexts of the protein. These reagents are iteratively contacted with the immobilized proteins on the array surface under conditions where binding can occur. Once the reagents bind to proteins on the array and background reagents are washed away, the bound affinity reagents may be detected, typically through a detectable label group associated with the affinity reagent, such as a fluorophore. Binding of the labeled affinity reagent at a given location on the array indicates the likely presence of the particular epitope in the protein at that location. By iteratively probing using different affinity reagents, and assessing the probability associated with the binding events, one can potentially characterize, or even identify, each protein that exists at each spot on the array. Moreover, by using affinity reagents that are not highly specific for an individual protein, but instead are capable of binding larger subsets of the proteome, e.g., multiple proteins containing a given trimer or tetramer epitope, one can potentially deconvolute a very large number of different proteins using a comparatively small number of affinity reagents. This "protein identification by short epitope mapping" (or "prism") approach is described in detail in U.S. Pat. Nos. 10,473,654B1, 11,545,234B1, and Eggertson, et al., A theoretical framework for proteome-scale single-molecule protein identification using multi-affinity protein binding reagents, bioRxiv, doi.org/10.1101/2021.10.11.463967, previously incorporated herein by reference.

In the context of characterizing proteins for proteoforms, antibodies may be targeted to larger epitopes that recognize protein structure which may be more than 3 or 4 amino acids, and may further include post-translational modifications, including phosphate groups.

FIG. 1 schematically illustrates an example of a protein analysis process and system using the Prism approach described above. As shown, a protein-containing sample 102 is obtained for analysis. Samples for analysis may be derived from any of a wide variety of biological systems, including animal, plant, microbial, viral, or the like. Moreover, samples may be derived from any of a variety of sources within a particular organism. For example, for animal-derived samples, samples may be obtained from tissue, e.g. as cells or cell lysates, organs, organoids, blood or plasma, or cerebrospinal fluids, or any other sources that may have protein profiles of biological interest.

In the context of an array-based approach for analysis, proteins in the sample are treated to attach individual protein molecules 104 to individual particles, such as structured nucleic acid particles or SNAPs 106. Once coupled to their respective SNAPs, the individual protein molecules are deposited and immobilized upon the surface of an array 108, where the SNAPs' size results in the individual protein molecules being sufficiently spaced apart that they can be analyzed separately upon the surface of the array.

For ease of illustration, arrays are shown with relatively small numbers of isolated proteins. However, it will be appreciated that an array surface may have upwards of 10s of thousands to 100s of thousands, to millions to billions of locations at which individual protein or polypeptide molecules may be located and separately interrogated/detected, e.g., 10,000 or more individual polypeptides, 100,000, or more individual polypeptides, 1,000,000 or more individual polypeptides, 10,000,00 or more individual polypeptides, 100,000,000 or more individual polypeptides, 1,000,000,000 or more individual polypeptides, or even 10,000,000,000 or more individual polypeptides on the surface of the arrays. Examples of this process and the resulting arrays are described in detail in, for example, U.S. Pat. Nos. 11,603,383B1, 11,505,795B1, WO 2023/102336A1, and Aksel et al., *High-density and scalable protein arrays for single-molecule proteomic studies*, bioRxiv doi.org/10.1101/2022.05.02.490328, the full disclosures of which are hereby incorporated herein by reference in their entirety for all purposes.

Once created, an array of individual protein molecules may be iteratively interrogated (shown in panel 110) with affinity reagents 112 that are capable of binding to relatively short epitopes within the proteins, e.g., trimer, tetramers or other short sequence contexts of amino acids. As noted previously, by utilizing affinity reagents that may bind to multiple proteins, but not all proteins, one can iteratively narrow down characteristics (e.g., identity, probability or probabilities of identity, quantity for the protein species, etc.) of a protein molecule at any given position based upon the pattern of affinity reagents that bind to the protein at that location. Moreover, one can also quantify the proteins on the array. As a result, one may be able to characterize tens of thousands of proteins with a far smaller number of affinity reagents than if one were to use only highly specific affinity reagents, e.g., affinity reagents that specifically bind to only one protein. Again, examples of this analytical approach are described in, for example, U.S. Pat. Nos. 10,473,654B1, 11,545,234B1, and Eggertson, et al., A theoretical framework for proteome-scale single-molecule protein identification using multi-affinity protein binding reagents, bioRxiv, doi.org/10.1101/2021.10.11.463967, previously incorporated herein by reference.

In the process, separate interrogation steps introduce different affinity reagents to the surface of the array, as shown in the expanded panel. These reagents are typically labeled, e.g., with fluorescent dyes, so that they may be detected. Following an incubation step to allow affinity reagents to bind to their specific target epitopes, excess reagents are washed away, and the surface of the array is scanned using a fluorescence detection system, e.g., a scanning fluorescence microscope, and those points on the array where the affinity reagents are bound are detected and recorded.

In some cases, different affinity reagents may carry differently detectable labels, e.g., fluorescent labels having different emission spectra, to allow simultaneous interrogation with 2, 3, 4 or more different affinity reagents. In these cases, the detection system will typically include optics, e.g., filters and directional components, that separate and separately measure signals having different spectral characteristics, thus allowing separate detection of the different affinity reagents bound to the array at the same time. Following multiple rounds of interrogation and scanning, the pattern of where different affinity reagents did and did not bind (schematically illustrated as observed binding measurement model 114), are used to "decode" the proteins in the array. These decoding processes typically utilize probability models (schematically represented as decoding 116) to assess likelihood of true and false positive and negative binding events to ultimately characterize the proteins and possibly identify (or determine probabilities of identification) the proteins. At the end of the process the quantities of each type of protein on the surface of the array may then be determined (as shown as quantitation readout 118 which depicts abundances for proteins EGFR, TP53, cMET, and PTEN), and ultimately extrapolated back to the quantity and/or identity of different proteins within the sample.

The decoding 116 process in FIG. 1 uses a probe probability binding model along with the observed binding measurement model 114 to generate quantitation readout 118. The probe binding probability model indicates estimated probabilities of the affinity reagents binding to candidate proteins that may be among the immobilized proteins on the array, or the predicted binding rates of probes to each type of protein. The probe binding probability model may be based on prior experiments, on-instrument measurements, off-instrument measurements, computationally generated, or a combination thereof.

However, the probe binding probability model is often imperfect, which can lead to inaccurate characterization of the proteins. For example, an inaccurate probe probability binding model results in an inaccurate determination of the quantities of the protein species that are immobilized on the array. As another example, an inaccurate probe probability binding model results in inaccurate identification of the immobilized proteins, or an inaccurate determination of the probabilities of identification of the immobilized proteins. An adaptive protein decoding approach, in which the probe probability binding model and protein quantity information are iteratively updated, results in incremental improvements of the accuracy of the protein quantities and the probe probability binding model.

Figure 2:
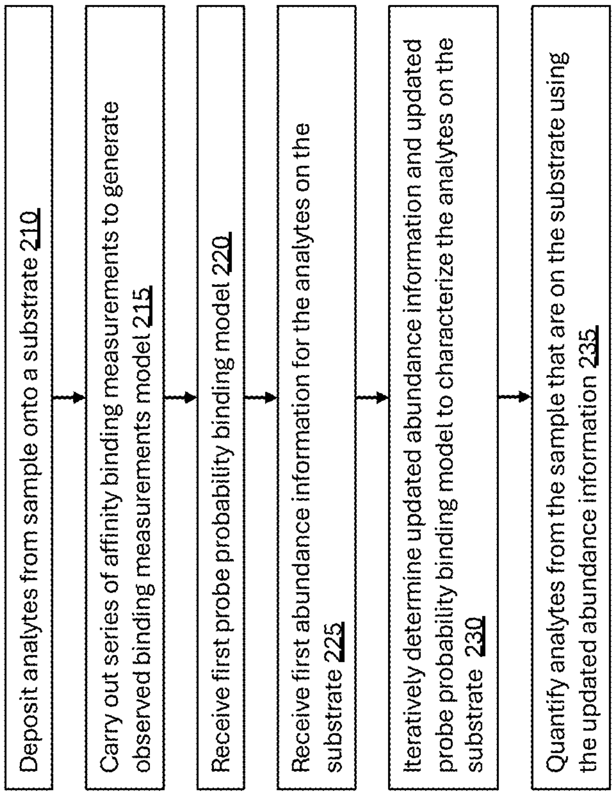
FIG. 2 illustrates an example of a flowchart for quantifying analytes via an iterative process.

For example, FIG. 2 illustrates a flowchart for quantifying analytes via an iterative process. In FIG. 2, analytes from a sample are deposited onto a substrate (210). For example, in FIG. 1, proteins from sample 102 are treated to attach individual protein molecules 104 to individual particles, such as structured nucleic acid particles or SNAPs 106, and deposited upon a surface of array 108.

Next, a series of affinity binding measurements is carried out to generate an observed binding measurements model (215). For example, in panel 110 of FIG. 1, affinity reagents 112 are iteratively applied to array 108 and to the immobilized proteins 104, unbound affinity reagents 112 are washed away, the bound affinity reagents 112 with the proteins 104 on SNAPs 106 are detected, the bound affinity reagents 112 are subsequently removed, and the process repeats with a different type of affinity reagent 112. The results of the detection are analyzed (e.g., via image processing) and an observed binding measurements model 114 is generated. As a result, observed binding measurements model 114 indicates positive measurement outcomes and negative measurement outcomes for the proteins 104 exposed to and interacting (e.g., binding or not binding) with different affinity reagents 112.

Figure 5:
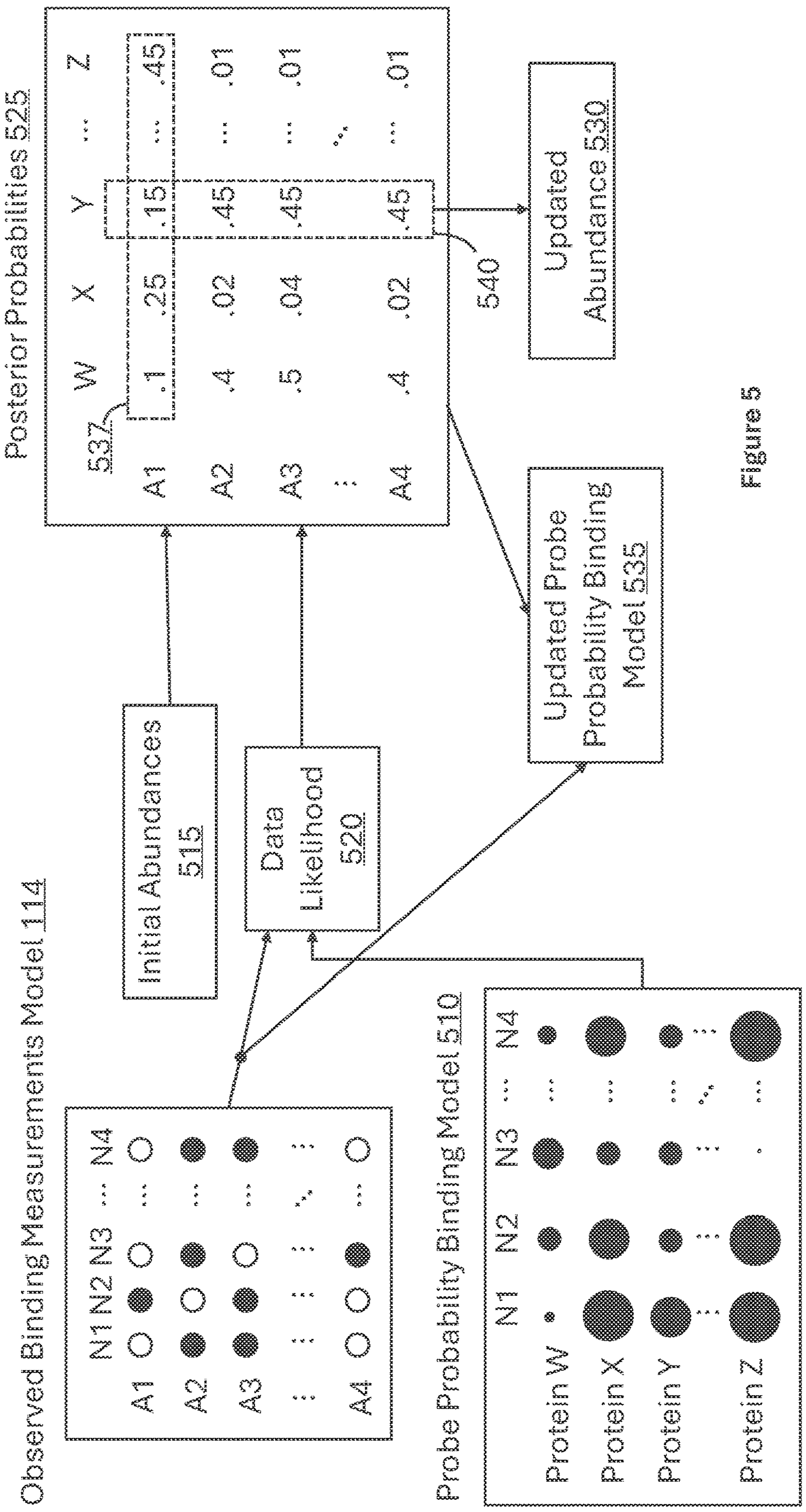
FIG. 5 illustrates an example of generating an updated abundance from an initial abundance, observed binding measurements, and a binding model.

Another visual representation of the observed binding measurements model 114 is shown in FIG. 5, which depicts an example of generating an updated abundance from an initial abundance, observed binding measurements, and a binding model. In FIG. 5, observed binding measurements model 114 is a matrix with immobilized proteins at locations A1-A4 of the array 108 and cycles N1-N4 of iteratively applying different affinity reagents 112 to the proteins. The filled circles represent that the affinity reagent applied in a cycle was observed to bind to the protein. By contrast, the empty circles represent that the affinity reagent applied in a cycle was observed to not bind to the protein.

For example, in cycle N1 where a first type of affinity reagent is applied, A1 was observed to not bind to the affinity reagent, but A2 was observed to bind to the affinity reagent. In the subsequent cycle N2, the opposite occurs. A1 is observed to bind to a second type of affinity reagent that was applied (i.e., a different affinity reagent than the one used in N1) but A2 is observed not to bind to the second type of affinity reagent. Thus, how each of the immobilized proteins on the array interacted with the affinity reagents applied through iterative cycles is recorded within observed binding measurements model 114.

Returning to FIG. 2, a first probe probability binding model is received (220) and a first abundance information for the analytes on the substrate or within the sample is received (225). For example, in FIG. 5, probe probability binding model 510 is obtained as an initial probe probability binding model to be used in the decoding techniques described herein. As visually depicted in the simplified example of FIG. 5, probe probability binding model 510 associates the probability that each of the affinity agents as probes applied in cycles N1-N4 bind to the particular candidate protein W-Z. That is, probe probability binding model 510 provides an initial estimate of probe-to-protein (or other analytes) binding, where each entry indicates a probability of measuring a binding event (e.g., as represented by observed binding measurements model 114) between a protein from a list of candidate proteins and a probe from a list of probes used to characterize the proteins. The values can represent numbers between 0-1, with 1 indicating a higher probability of binding and 0 indicating a lower probability of binding in some implementations.

In FIG. 5, a larger circle indicates a higher probability of binding than a smaller circle. For example, candidate protein W is shown to have a lower probability of binding with the affinity reagent applied to the array during cycle N1. However, in N3, the same candidate protein W is shown to have a higher probability of binding with the affinity reagent applied to the array during cycle N3. The probe probability binding model 510 has an entry for each candidate protein that might be within the sample and, therefore, immobilized upon the array. Thus, each candidate protein has its own row within a matrix, and each cycle has its own column, with the data indicating the probability of the affinity reagent of the cycle binding with the corresponding candidate protein.

As also depicted in FIG. 5, initial abundances 515 for the sample and, therefore, the immobilized proteins on the array, is also obtained. Initial abundances 515 provide an initial estimate for the quantities of the proteins in the sample. In some implementations, initial abundances 515 indicate a uniform distribution of all possible protein candidates within the sample. That is, each of the candidate proteins W-Z (e.g., 4 proteins, 20 proteins, 2000 proteins, 20000 proteins, etc.) has an equal abundance with the other candidate proteins W-Z. Thus, if there are 10 billion proteins within the sample, then the 10 billion proteins would be uniformly assigned to the candidate proteins such that each of the abundances of the candidate proteins is equal (or within a relatively tight range, such as less than 1% differences) with each other.

However, in other implementations, non-uniform distributions can also be used for initial abundances 515. For example, if the sample is a plasma sample, one would expect a higher abundance of albumin proteins and, therefore, initial abundances 515 can be non-uniform with albumin having a larger initial abundance than other candidate proteins. Therefore, the source or the type of sample (e.g., blood plasma, tissue, type of cells, animal species, organ, age, etc.) can be determined or received and an appropriate non-uniform distribution can be set to the initial abundances. Likewise, rare proteins in a sample may be represented by a lower initial abundance than other candidate proteins in initial abundances 515. Similarly, proteins that are unlikely to appear in the sample may also be represented by a lower initial abundance.

Returning to FIG. 2, an iterative determination of updated abundance information and an updated probe probability binding model is performed to characterize the analytes on the substrate (230). In some implementations, the iterative determination is based on an implementation of an Expectation-Maximation (EM) technique for a Bernoulli finite mixture. The EM technique is described by Dempster et al., *Maximum Likelihood from Incomplete Data Via the EM Algorithm*, Journal of the Royal Statistical Society: Series B (Methodological), Volume 39, Issue 1, September 1977, pages 1-22, doi.org/10.1111/j.2517-6161.1977.tb01600.x, which is hereby incorporated by reference in its entirety for all purposes. In some implementations, the EM technique may utilize Poisson binomial distribution principles.

In particular, the EM technique includes performing an expectation step (or E-step) and then a maximization step (or M-step) is performed. After the first iteration of performing an E-step and an M-step, another iteration of an E-step and M-step is performed with the new results obtained from the prior iteration's E-step and M-step outputs. This process of iteratively performing E-steps and M-steps, with the output of a prior iteration providing new data for subsequent iterations, is performed repeatedly until convergence, which means that the converged solution provides estimates that more accurately reflect ground truth values. In the context of the problem of decoding the proteins immobilized on the array, the ground truth values include the abundances of the protein species immobilized on the array, and/or identifying information, and/or the probe probability binding model.

Specifically, in the E-step, identification information indicating probabilities that an immobilized protein is each of the candidate proteins is determined given the observed binding measurement model. These probabilities are also known as posterior probabilities, and within the context of the EM technique are known as latent variables. The output of the E-step is referred to as a model parameter and can include abundance information to quantify the immobilized proteins in terms of the candidate proteins. As discussed later, the identity of each immobilized protein is fractioned into "pseudocounts" (or responsibilities) as abundances that are in proportion to the probabilities and to serve as identification information. The pseudocounts for each of the candidate proteins is then summed and used to determine the abundances to assign to each of the candidate proteins. That is, one of the outputs of the E-step is an estimate of the quantitation of the immobilized proteins.

In the M-step, maximum-likelihood estimates of the probe probability binding models is determined for each of the candidate proteins with the pseudocounts used in the E-step serving as the identities of the immobilized proteins. The output of the M-step is also referred to as a model parameter. The newly determined probe probability binding model is therefore a better interpretation of the observed binding measurements model than the initial probe probability binding model. The E-step and M-step iterations repeat to provide more accurate abundances and probe probability binding models generated that are closer to the ground truth than the initial abundances and initial probe probability binding model given the observed binding measurement model. Thus, the implementations described herein perform an iterative process with two steps: the first step updates abundances while keeping the probe probability binding model fixed, and then the second step updates the probe probability binding model while keeping the abundances fixed. In some implementations, the two steps may be performed in parallel; for example, the updated abundant information and the updated probe probability binding model can be updated by considering the latest identification information (or posterior probabilities).

Figure 3:
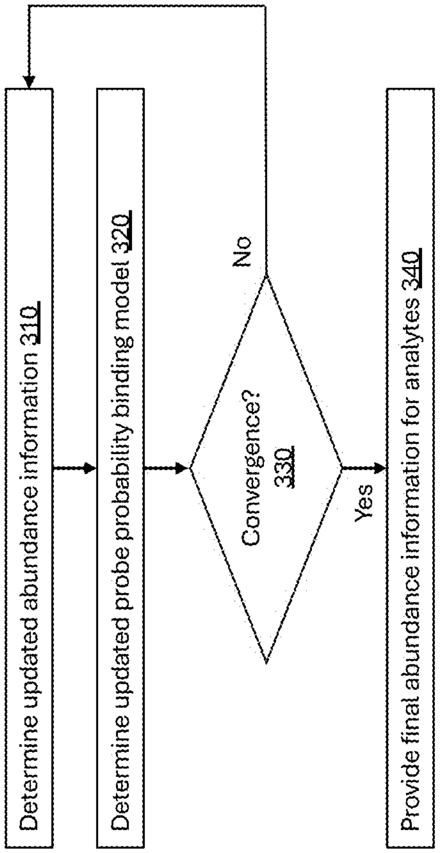
FIG. 3 illustrates an example of a flowchart of an iterative process used to quantify analytes and update a binding model.

FIG. 3 depicts an example of a flowchart for quantifying analytes via an iterative process. The iterative process depicted in FIG. 3 shows that updated abundance information is determined (310). Returning to FIG. 5, updated abundance 530 is the updated abundance information for candidate protein Y. To obtain this updated abundance, first an intermediate determination regarding data likelihood 520 is determined based on observed binding measurements model 114 and probe probability binding model 510. Data likelihood 520 represents the likelihood that the observed binding measurements for an immobilized protein (e.g., immobilized protein or array location A1 in observed binding measurements model 114) would be produced by a candidate protein indicated in the probe probability binding model 510. The data likelihood 520 and initial abundances 515 are then used to determine posterior probabilities 525 via an application of Bayes' theorem. For example, the posterior probabilities 525 determine the likelihoods for the data likelihood 520 (which represents the likelihood or probability that the observed binding measurements would be produced by a candidate protein) in view of the initial abundances 515. The calculations for these operations are described in an example later herein.

In the example of FIG. 5, posterior probabilities 525 is represented as a matrix with values between 0-1. Each value in posterior probabilities 525 is calculated using the current estimate of abundances and the data likelihood. This results in each immobilized protein contributing a single count (or unitary or single value) to the overall abundance of all the proteins immobilized on the array, but fractioned, split, or divided into "pseudocounts" as abundances that are in proportion to the probabilities for each of the candidate proteins. For example, for immobilized protein A1, the total sum of all the values in row 537 would equal 1. Thus, the identity of immobilized protein A1 has been divided into pseudocounts across the candidate proteins W-Z, such as 0.1 for candidate protein W (i.e, 10% probability to be candidate protein W), 0.25 for candidate protein X (i.e., 25% probability to be candidate protein X), 0.15 for candidate protein Y (i.e., 15% probability to be candidate protein Y), and so on until 0.45 for candidate protein Z (ie . . . , 45% probability to be candidate protein Z). Each of the immobilized proteins includes pseudocounts for the various candidate proteins W-Z. In some implementations, the posterior probabilities 525 is referred to as an identity indicator matrix.

To calculate the abundance of a specific protein, for example, candidate protein Y, the pseudocount values in column 540 are summed to provide updated abundance 530 which represents the abundance for protein Y among the immobilized proteins on the array. An updated abundance is calculated for each of the candidate proteins (e.g., for candidate proteins W-Z) to provide the separate abundances of all the immobilized proteins on the array. As such, the E-step of the EM technique provides the updated abundance information for the proteins. Additionally, the E-step provides identity information in terms of the pseudocounts distributed across the candidate proteins for each immobilized protein. In some implementations, the updated abundances for all the candidate proteins are referred to as a prior within the context of the EM technique.

Though many of the examples described herein use pseudocounts, other approaches to determine the updated abundance information in the E-step may be used. For example, a "winner-takes-all" approach in which the highest probability or pseudocount is selected among the candidate proteins to identify the immobilized protein. The quantitation of the proteins would then be the result of a summation of the assigned protein identities for each of the locations. In another example, a threshold may be applied. If the probability or pseudocount is above a specific number or within a certain range, then the immobilized protein is assigned the identity corresponding to the candidate protein with the highest probability or pseudocount in the range or above the threshold and a summation of the assigned identities would be performed to quantify the immobilized proteins. If for a particular immobilized protein, the posterior probabilities 525 does not have a value above the threshold or within the certain range, then that specific immobilized protein may be excluded from contributing to the updated abundance.

In some implementations, the updated abundance may be restrained within a threshold range to account for candidate proteins that are usually within a threshold range of a sample. For example, in some samples, specific proteins are expected to be within a particular abundance or percentage of total abundance of all proteins contained in the sample. Thus, as the updated abundance information is updated through multiple iterations, the abundance may be restrained to the threshold range. This restraint on abundances allows for more accurate and stable updated abundance information. Thus, the updated abundance information is restrained based on a prior distribution, and that restraint can be based on a mean and/or a variance for the abundance of the specific protein in relation to the threshold range.

Returning to FIG. 3, the updated binding model is then determined (320). For example, in FIG. 5, the updated probe probability binding model 535 is determined using posterior probabilities 525 and observed binding measurements model 114. This represents an implementation of the M-step of the EM technique. In particular, the pseudocounts of the posterior probabilities 525 are used as identification information of the immobilized proteins. For example, for A1 in posterior probabilities 525, the values are in proportion to the probabilities as previously noted. As previously noted, this deviates from a "winner-takes-all" approach in which a singular, unambiguous identification of a protein is made. Rather, identification information of a protein is based on the pseudocounts across the various candidate proteins though the "winner-takes-all" approach may also be used.

The posterior probabilities 525 and observed binding measurements model 114 are then used to determine and acquire an updated probe probability binding model 535. The values of the updated probe probability binding model are determined by maximizing (or increasing) the likelihood or probability of observing the values in the observed binding measurements model 114 given the posterior probabilities 525 (which is based on the probabilities of the abundances, observed binding measurements model, and binding models as previously described). For example, the binding measurements observed for an immobilized protein across multiple cycles is used to assign possible identities to the protein (as indicated in posterior probabilities 525). The correspondence of the proteins and their binding status to the probe (bound or unbound) and the probabilities indicated in posterior probabilities 525 are considered to determine a binding rate or value for the updated probe probability binding model. If a definitive identification is made for each protein rather than probabilities of posterior probabilities 525, then an estimate for a binding rate for a probe X to a protein Y would be the fraction of times a binding event was observed for the probe X for all immobilized proteins identified as protein Y. However, the technique herein accounts for probabilistic identifications by summing the values in the posterior probabilities 525 for binding and non-binding events, and calculating the binding rate as the binding value divided by the sum of the binding and non-binding values.

Thus, a value of the updated probe probability binding model representing the probability of one type of probe to bind with one type of candidate protein is based on the number of positive binding measurements that were observed (as indicated in the observed binding measurements model) and the corresponding values in posterior probabilities 525 to account for a pseudocount approach, assuming that a "1" value represents a positive binding measurement. These values are summed and then divided by the sum for both "1" and "0" values to provide a new value for a candidate protein to a probe type (or cycle). The calculations to perform this are located later herein.

In some implementations, values of the updated probe probability binding model may be restrained within a threshold range to account for known or expected probabilities of probes binding to proteins. Thus, a prior distribution of the probe probability binding model is used to restrain the updated probe probability model. This is discussed more later herein regarding beta distributed priors.

Returning to FIG. 3, a check for convergence is determined (330). Convergence can be reached by determining that a certain number of iterations has been performed, one or more values has been updated by less than a threshold amount for a fixed number of iterations (e.g., less than 1% changes for any values of the updated abundances or updated probe probability binding model after 4 iterations), though other convergence conditions can be used. Thus, if convergence is not reached, then the iteration proceeds back to determining updated abundance information again (310) and updated probability binding model (320). If convergence is identified, then the final abundance information for analytes is provided as the abundances (340). Thus, returning to FIG. 2, this updated abundance information is used to quantify the analytes from the sample that are on the substrate (235). That is, the updated abundance information received via the adaptive protein decoding process, in an iterative fashion, is used as the quantitation of the proteins in the sample by refining the probe probability binding model. Any of the data used to characterize the immobilized proteins, including the finally determined quantitation of the proteins in the sample, identification information (e.g., protein identifications or probabilities of identification), probe probability binding model, etc. may be stored in memory and retrieved for further analysis.

If the probe probability binding model 510 that is used in the first iteration is sufficiently accurate to drive convergence to the ground truth (i.e., the actual abundance of proteins on the substrate), then values is posterior probabilities 525 might be off. However, the refining or adapting of the updated probe probability binding models through multiple iterations, even with the inaccurate posterior probabilities 525, can lead to improved characterization of the proteins. For example, more accurate quantitation, identification information, or other information regarding the proteins is achieved. Moreover, because many of the calculations may be performed in matrix multiplication, less computing resources may be employed to analyze the vast amount of data utilized by the iterative process.

Figure 4:
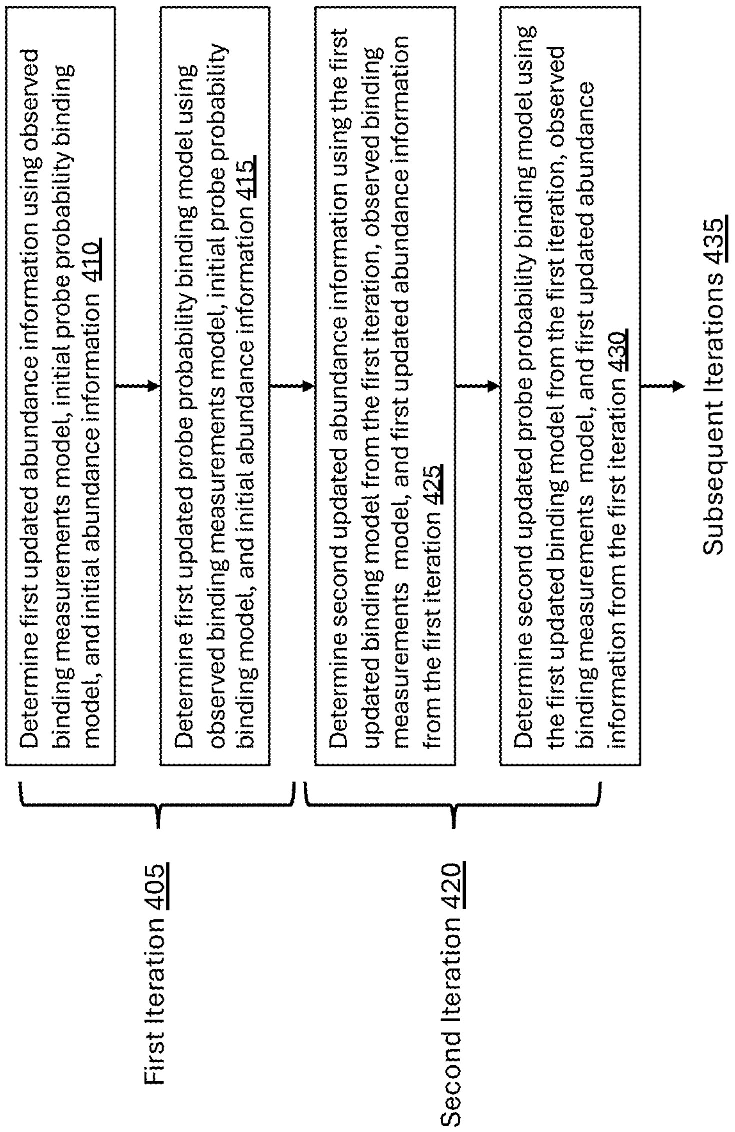
FIG. 4 illustrates another example of a flowchart of an iterative process used to quantify analytes.

Another example of the iterative process is depicted in FIG. 4. In FIG. 4, two iterations are depicted: first iteration 405 and second iteration 420. In the first iteration 405, first updated abundance information is determined (410). This is based on the observed binding measurements model (e.g., observed binding measurements model 114 in FIG. 5), initial probe probability model (e.g., probe probability binding model 510 in FIG. 5), and initial abundance information for the proteins in the sample (e.g., initial abundances 515 in FIG. 5) used to generate protein identification information (e.g., posterior probabilities 525) and the pseudocounts may be summed to provide the first updated abundance information. The updated abundance information is an incremental improvement that is closer to the ground truth (i.e., the true abundances in the sample) than the initial abundances 515.

Next, in FIG. 4, the first updated binding model is determined. For example, if posterior probabilities 525 in FIG. 5 are calculated based on the observed binding measurements model 114, probe probability binding model 510, and initial abundances 515, then the binding rates may be generated as updated probe probability binding model 535, as previously discussed. The first updated binding model is closer to the ground truth than the initial probe probability binding model 510. Thus, initial data for the probe probability bindings and initial abundances are used in the first iteration, but updated upon completion of the first iteration by generating new probe probability bindings and abundance information.

In FIG. 4, the second iteration then begins. As depicted, second updated abundance information is determined using the first updated probe probability binding model from the first iteration's M-step, the observed binding measurements model 114, and the first updated abundance information from the first iteration's E-step (425). For example, the first updated probe probability binding model and the first updated abundance information are used to determine new identification information such as posterior probabilities 525. The new identification information is then used to determine the updated abundance information in a manner similar as previously discussed. Next, a second updated probe probability binding model is determined based on the new identification information as well (430). Thus, initial abundances 515 and an initial probe probability binding model 510 are used in the first iteration, but subsequently replaced with updated versions in the second iteration. As previously discussed, subsequent iterations 435 are performed until a convergence condition is satisfied.

Accordingly, the first iteration 405 utilizes initial values for the probe probability binding model and abundance. However, these values are changed after the first iteration and the newly updated values are used in the subsequent iterations. However, the observed binding measurements model 114 is used in every iteration and does not change as it represents the observed measurements (i.e., the immobilized proteins exposed to affinity reagents).

Many of the implementations described herein use matrices to represent various forms of information used in calculations. In other implementations, the information may be represented in other forms. Moreover, the interaction between the affinity reagents and the immobilized proteins is described as observed. Though visual observation may be performed (e.g., by using a camera detecting excitation of fluorophores or dyes), other non-visual forms of detection may also be performed to generate the observed binding measurements model 114.

In some implementations, updated abundance 530 may be determined, but updated probe probability model 535 may not be updated. Thus, each iteration may generate updated abundance 530 while using the original probe probability binding model 510. In other implementations, updated probe probability binding model 535 may be generated in some iterations, for example, every other iteration, every 4 iterations, only the first iteration, only the last iteration, a middle iteration between the first and last iterations, etc. This may result in fewer computational resources necessary to perform the techniques described herein.

The techniques described herein involve quantifying proteins of protein species. However, the same techniques can be used to quantify various properties of a protein species. For example, one type of protein (e.g., Tau, alpha-synuclein, etc. proteins) may have many different proteoforms (e.g., different phosphorylation sites or different isoforms). The immobilized proteins may be Tau proteins and the techniques described herein may be employed to quantify different proteoforms of Tau protein. For example, the candidate proteins described herein may be candidate proteoforms or proteoform groups (i.e., groups of post-translational modifications at selected epitopes). Thus, Tau proteins may be enriched and then immobilized as the immobilized proteins. Iterative rounds of probing may be performed, observed binding measurements model 114 may be generated, a probe probability binding model 510 may be acquired, and data likelihood 520 may be generated for the candidate proteoforms. In some implementations, for proteoform characterization, the probe probability binding model 510 may include both on-rates and off-rates for each of the probes to specific or candidate epitopes of the protein species. For example, for a candidate epitope, a probe may have an 80% probability of binding and 3% for not binding as detailed in the probe probability binding model 510. The probe probability binding model 510 with the on-rates and off-rates is then used to determine PTMs for each of the proteins on the array, similar to the techniques previously described. Proteins with similar post-translational modifications (PTMs) are then identified and grouped to quantify proteoform candidates. For example, one protein may have 1 phosphorylated site at epitope A, another protein may have a phosphorylated site at epitope B, another protein may have phosphorylated sites at epitopes A and B, and another protein may have a phosphorylated site at epitope C. These different groupings would be identified as different proteoform groupings of the protein species.

Initial abundances 515 (for the abundances of proteoforms) and data likelihood 520 are then used to generate posterior probabilities 525 in a similar manner as described herein, except with candidate proteoforms rather than candidate proteins. That is, posterior probabilities 525 may then represent the probability that each candidate proteoform corresponds to the observed binding patterns. Updated abundances and binding rates may also be generated in a similar manner.

In some implementations, some or all of the probability values in the first probe probability binding model are based on depositing single recombinant proteins in a first lane of a flow cell and depositing the proteins from the sample in another, second lane of the flow cell. Observed binding measurements of the single recombinant proteins in the first lane can be obtained similarly as described herein and used to generate some or all of the probability values. In some implementations, the probability values may be based on probe probability binding models generated from single recombinant proteins used in previous experiments (i.e., from other flow cells other than the one that the proteins of the sample are deposited upon).

Figure 8:
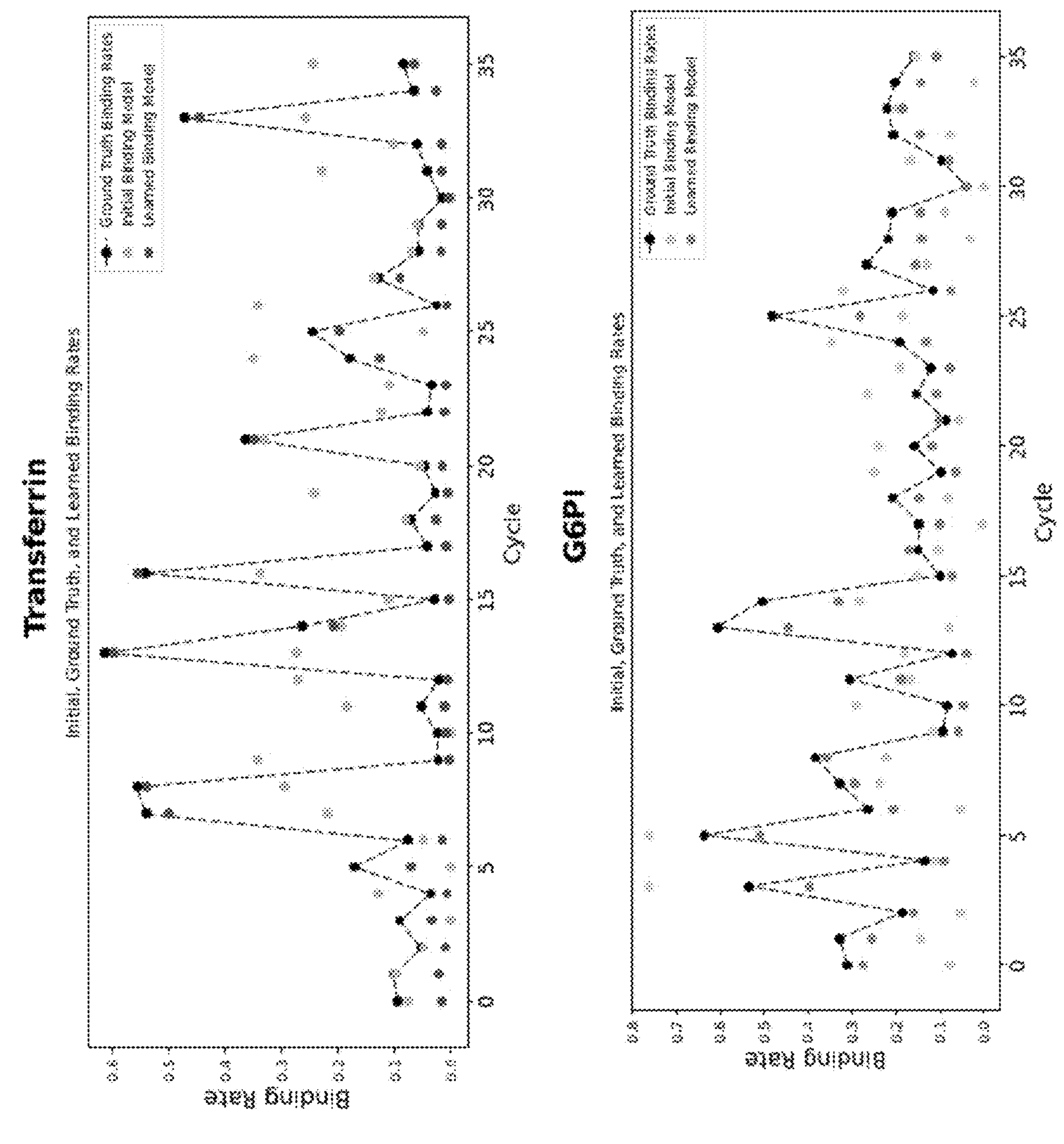
FIG. 8 shows examples of the results of analyte characterization via an iterative process.

FIG. 8 shows examples of results of analyte characterization via an iterative process. In FIG. 8, the ground truth binding rates are compared with the initial binding model and the learned, or updated, probe probability binding rates using the techniques described herein. The learned rates were derived from binding data from a mixture sample containing Transferrin, G6PI, and Model Protein. Ground truth rates are measured from a single-protein control lane.

FIG. 9 shows an example of the results of analyte characterization via an iterative process. In FIG. 9, samples containing single proteins (G6PI, Transferrin, or a Model Protein) were decoded using the techniques described herein. The fraction of molecules identified and/or quantified for each of the three possible proteins is shown in FIG. 9. The decoding techniques described herein reduced false positives of protein identifications and/or quantitation compared to a decoding method that does not use the iterative process described herein.

More information related to proteoforms and their analysis is described in: Provisional U.S. Patent Application No. 63/676,145, filed on Jul. 26, 2024, Provisional U.S. Patent Application No. 63/687,689, filed on Aug. 27, 2024, and Provisional U.S. Patent Application No. 63/709,289, filed on Oct. 18, 2024, the full disclosures of which are hereby incorporated herein by reference in their entirety for all purposes.

In some implementations, full-length proteins may be identified and immobilized proteins that are not full-length may be discarded from the analysis. For example, in a final round of iterative probing, a probe that can be used to recognize any of the candidate proteins may be used.

In some implementations, as the probe probability binding model is updated, a "steric factor" may be applied to prevent the binding models from merging due to overfitting. For example, the probability binding models may be updated as described herein, but may merge with each other and converge even when a candidate protein does not exist as one of the immobilized proteins. To prevent this, the similarity (or dissimilarity) between the binding rates of the different candidate proteins may be determined, for example, using the Jensen-Shannon divergence. The amount of the similarity is then used to modify the binding rates such that they will not merge. The larger the similarity, the greater the modification of the binding rates (e.g., adding or subtracting a scaling factor based on the similarity).

In some implementations, the pseudocounts technique described herein is used to characterize and/or quantify the candidate proteins or the candidate proteoforms. In other implementations, the winner-takes-all approach technique described herein is used to characterize and/or quantify the candidate proteins or the candidate proteoforms. In some implementations, the pseudocount technique may be used to characterize and/or quantify candidate proteoforms, and the winner-takes-all technique may be used to characterize and/or quantify candidate proteins, or vice versa. In some implementations, characterization of proteins or proteoforms includes quantitation without an assigned or unambiguous identification of proteins or proteoforms. However, in other implementations, a specific identification of the protein or proteoform may be assigned.

As alluded to above, the present disclosure provides for the various reagents used in the herein described methods and systems. For example, included herein are affinity reagents, and combined libraries of affinity reagents that have relatively high affinity for specific characteristics of different proteoforms of a given protein of interest. These reagents may include antibodies, antibody fragments, aptamers, binding proteins, binding peptides, or the like that are capable of specifically binding to a given characteristic of a proteoform of the protein of interest. In particular aspects, the affinity reagents may include detectably labeled antibodies or binding fragments of antibodies, such as fluorescently labeled antibodies. These libraries are typically stored in multi-well plates or other similar storage vessels where each different reagent is separately stored from the other. In some cases, multiple different reagents may be stored within the same container where they may be differentiated during detection, e.g., through detectably different fluorescent labels attached to the different reagents, e.g., different fluorescent labels having different emission spectra.

Figure 6:
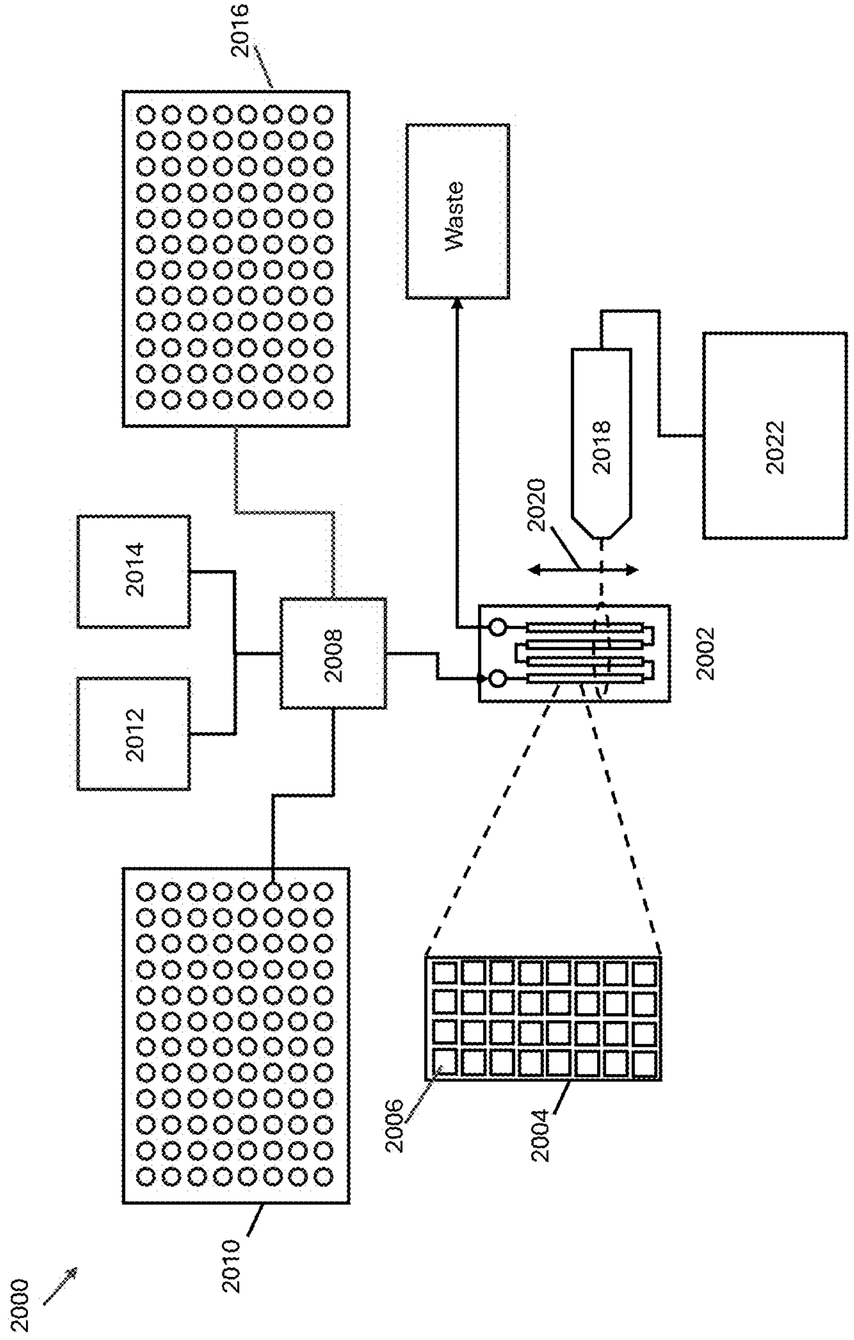
FIG. 6 illustrates an example of a system for quantifying analytes and updating a binding model.

As also noted above, provided herein are systems for quantifying analytes and updating a binding model. An example of such a system is illustrated in FIG. 6. As shown, the system 2000 includes a flowcell 2002 that includes an array surface (shown as 2004) within the channels of the flow cell upon which individual protein molecules from a sample may be deposited and immobilized in locations 2006 that are individually addressable, and in particular cases are individually optically resolvable from each other using, e.g., fluorescence microscopy or scanning techniques.

The system will also typically include a fluidic delivery system 2008 that is configured to deliver different fluids to the flow cell 2002 through a series of fluidic lines and utilizing appropriate pumps, valves and other conventional fluid controls. The fluidics system 2008 may be fluidically coupled to various sources of fluids and reagents needed to carry out the analysis on the flow cell. For example, as shown, fluidic system 2008 is fluidly coupled to a source of a plurality of reagents 2010 (shown as a 96-well plate, although any number of different reagent storage systems of varying capacity may be employed) that includes a library of multiple affinity reagents that each have affinity for different characteristics of one or more proteins of interest. Additionally, fluidic system 2008 may also be coupled to sources of washing fluids or buffers 2012, and removal reagents 2014 (for removing bound affinity reagents following detection), as well as any other ancillary fluids and reagents needed for the analysis. Similarly, where flow cells are prepared on the system, the fluidic system may be coupled to sources of different sample materials that are to be analyzed 2016

(again, shown as a 96-well plate, although again, any suitable sample storage system or capacity may be suitable).

The reagent sources are typically fluidly connected to the flow-cell using fluidics systems that can separately access different reagents, sample materials and other fluids, and control the timing and volume of different reagents delivered to the flow-cell at different times in order to carry out the deposition, interrogation, washing and removal steps of the analysis process. Such fluidic systems will typically include requisite valves and pumps for carrying out such fluid deliveries and include, for example, those as described in, for example, International Patent Application No. WO 2023/122589A2, the full disclosure of which is hereby incorporated herein by reference in its entirety for all purposes.

The systems described herein also typically include a detection system, such as optical detection system 2018, for detecting and recording fluorescent signals arising from different positions on the array surface. Such detection systems may generally include line scanning confocal fluorescent microscope systems, which are capable of scanning across large array surfaces (as shown by arrow 2020) to detect and record fluorescence across such surfaces at reasonably high scan rates.

The overall systems also typically include one or more computers or processors 2022 for controlling the operation of the instrument system including the fluidic system 2008 (e.g., to sample different sample sources 2016, reagent sources 2010 and delivery timing and volume of each), and detection system 2018, among other functions, and for recording the detected signals received from the detection system 2018, e.g. fluorescent signals, and analyzing such signals to identify potential binding by each of the different affinity reagents. Processors 2022 also have access to memory storing instructions that are executed to perform any of the techniques described herein. Included in such memory may be bioinformatic software or firmware that evaluates the signals received and based upon appropriate modeling, identifies likely positive binding events, and then subsequently provides an overall assessment of characteristics of the proteins as described herein including identification information of proteins that are present at any given location on the array as well as the relative abundance of each different protein across the array and ultimately, within the sample being analyzed. Examples of bioinformatic software processes for analyzing such proteoform and proteome data have been described in, for example, U.S. Pat. Nos. 11,545,234, 10,473,654B1, and Eggertson, et al., *A theoretical framework for proteome-scale single-molecule protein identification using multi-affinity protein binding reagents*, bioRxiv, doi.org/10.1101/2021.10.11.463967, U.S. Patent Application No. 2022/0236282, International Patent Application Nos. PCT/US24/15132, and WO 2023/038859. Alternatively, in some cases, recorded data from the binding events, stored as digital information, digital image files, or compressed versions of such image files, may be transmitted to separate servers or cloud based systems, which house the informatics software that performs this latter analysis and reporting.

Figure 7:
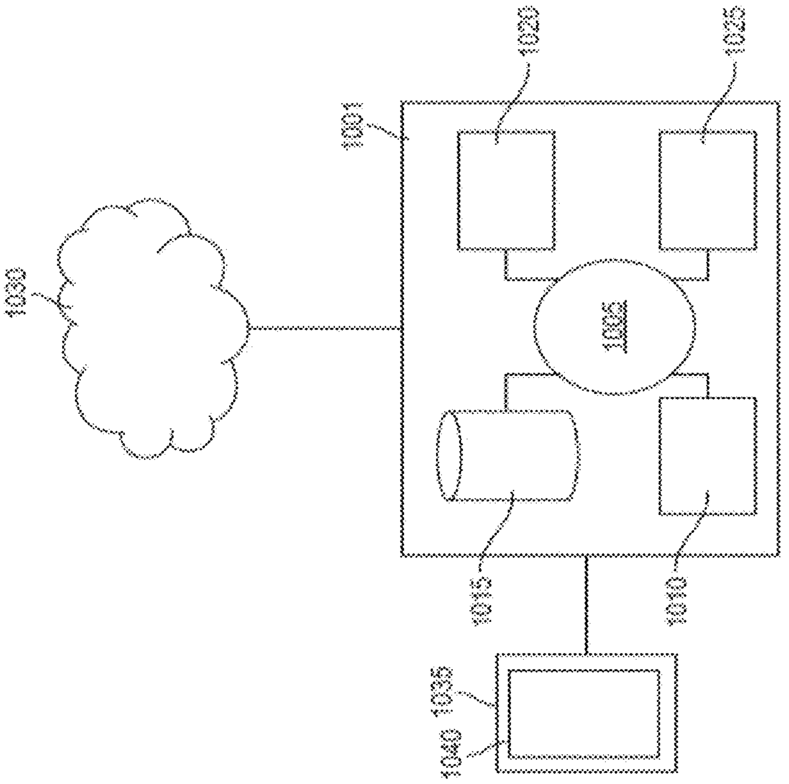
FIG. 7 illustrates an example of a computing system used to perform techniques, including an iterative process used to quantify analytes.

FIG. 7 illustrates an example of a computing system used to perform techniques, including an iterative process used to characterize analytes. In FIG. 7, the computer system 1001 can be an electronic device of a detection system, the electronic device being integral to the detection system or remotely located with respect to the detection system. For example, the computer system 1001 can be the computer system 2022 of FIG. 6. In another example, the electronic device can be a mobile electronic device. The computer system 1001 includes a computer processing unit (CPU, also "processor" and "computer processor" herein) 1005, which can be a single core or multi-core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an intranet and/or extranet, or an intranet and/or extranet that is in communication with the Internet. The network 1030, in some cases, is a telecommunication and/or data network. The network 1030 can include one or more computer servers, which can enable distributed computing, such as cloud computing. For example, one or more computer servers may enable cloud computing over the network 1030 ("the cloud") to perform various aspects of analysis, calculation, and generation of the present disclosure, such as, for example, receiving information of empirical measurements of extant glycans in a sample; processing information of empirical measurements against a database comprising a plurality of candidate glycans, for example, using a binding model or function set forth herein; generating probabilities of a candidate glycan generating empirical measurements, and/or generating probabilities that extant glycans are correctly identified in the sample. Such cloud computing may be provided by cloud computing platforms such as, for example, Amazon Web Services® (AWS), Microsoft Azure®, Google Cloud Platform®, and IBM® cloud. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android®-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, user selection of algorithms, binding measurement data, candidate proteins, and databases. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, receive information of empirical measurements of extant proteins in a sample, compare information of empirical measurements against a database comprising a plurality of protein sequences corresponding to candidate proteins, generate probabilities of a candidate protein generating the observed measurement outcome profile, and/or generate probabilities that candidate proteins are correctly identified in the sample.

The present disclosure provides a non-transitory information-recording medium that has, encoded thereon, instructions for the execution of one or more steps of the methods or techniques set forth herein, for example, when these instructions are executed by an electronic computer in a non-abstract manner. This disclosure further provides a computer processor (i.e. not a human mind) configured to implement, in a non-abstract manner, one or more of the methods set forth herein. All methods, compositions, devices and systems set forth herein will be understood to be implementable in physical, tangible and non-abstract form. The claims are intended to encompass physical, tangible and non-abstract subject matter. Explicit limitation of any claim to physical, tangible and non-abstract subject matter, will be understood to limit the claim to cover only non-abstract subject matter, when taken as a whole. Reference to "non-abstract" subject matter excludes and is distinct from "abstract" subject matter as interpreted by controlling precedent of the U.S. Supreme Court and the United States Court of Appeals for the Federal Circuit as of the priority date of this application.

An example regarding the adaptive protein decode technique is now described.

The adaptive protein decode technique described above refers to a technique that estimates two quantities that characterize a proteomic sample and the platform used in this characterization.

The first quantity is the relative abundances of different types of SNAPs in a prepared sample derived from a biological sample containing proteins. As previously noted, SNAP refers to the "structured nucleic acid particle" to which single molecules of protein are conjugated. Single SNAPs are immobilized on discrete sites in a lattice on the surface of a flow cell, allowing analysis of single molecules of immobilized protein. SNAP type is defined by the identity of the protein conjugated to it or the absence of a protein. The presence of SNAPs with no protein—NULL SNAPs—are not a desired feature of the assay but rather reflects a limitation in sample-prep capability that should be addressed by the adaptive decode process described herein.

The method is designed to "identify"—i.e. infer the identity of—individual SNAPs and then report relative abundances of SNAP types (i.e. as a proxy for protein abundances) according to the principle of "quantification by counting". Uncertainty in the identification of each individual SNAP can be addressed by assigning fractional pseudocounts to each potential identity for that SNAP.

The second quantity estimated by the adaptive decode method is the on-platform detection of binding between a defined collection of probes or lobes—a portmanteau for "labeled probes"—and a defined set of candidate SNAP types—i.e. identified by a defined set of protein plus the NULL SNAP type.

Adaptive Decode is an extension of another problem, which will be referred to as Ideal Decode. The Ideal Decode problem has been constructed to provide a best-case scenario for characterizing a simple mixture of SNAPs (i.e., immobilized proteins when deposited on the array) that provides the best possible result. Ideal Decode corresponds to a platform with idealized behavior, where certain strict assumptions must be met. It is useful to describe Adaptive Decode in terms of Ideal Decode, specifically identifying those assumptions that are not required for Adaptive Decode, given its improved analytical capabilities.

The ability of the platform to characterize a proteomic sample is predicated on (i) differences in detected binding across the collection of lobes for each of the defined SNAP types, and (ii) the ability to characterize or model the detected binding of each lobe to each defined SNAP type.

In an ideal realization of the platform, one would characterize the detected binding for each (SNAP-type, lobe) pair in advance of analyzing biological samples. The characterization process would involve constructing a binding model matrix (or probe probability binding model as described elsewhere herein), where each row represents a SNAP type (or candidate proteins as described elsewhere herein) and each column represents a distinct lobe type (or probe or affinity reagent as described elsewhere herein.

In an example operation of the idealized platform, twelve rows of the binding model matrix can be filled in a single run. In each of twelve lanes—three flow cells run in parallel, where each flow cell has four lanes—a homogenous population of molecules of a single SNAP type would be deposited on the flow cell surface and interrogated by the set of lobes in sequential cycles, one lobe at a time, recording whether or not binding was detected in each cycle.

The elements of the binding model matrix are the fraction of SNAPs where binding was detected for each (SNAP type, lobe type) pair or equivalently each (flow cell lane, cycle) pair. We sometimes refer to the fraction of SNAPs where binding is detected as a binding "rate". In this usage, rate refers to the frequency of a detected binding outcome in a homogeneous population, rather than a characterization of the time-dependent features of binding.

In this idealized realization of the platform, the binding model matrix would be determined by running the entire collection of proteins (e.g. human proteome) on the platform, twelve proteins at a time.

To characterize a biological sample as a mixture of these proteins and their relative abundances in SNAP types—as a proxy for their abundances in the original biological sample, one would compare the observed binding measurements (or observed binding measurements model as described elsewhere herein) to the binding model matrix. The analysis represents a deconvolution problem.

In the idealized realization described here, the detected binding of lobes to proteins observed in biological samples would not vary from the detected binding in the experiments used to construct the binding model matrix. In other words, the system would have perfect reproducibility in the detected binding rates for every (SNAP type, lobe type) pair.

In this idealized realization, there would be no need for the Adaptive Decode method described in this document. However, Adaptive Decode extends the capabilities of Ideal Decode to address practical (non-ideal) protein identification.

Adaptive Decode addresses two practical considerations in using the platform to characterize biological samples: (1) the detected binding for (SNAP type, lobe type) pairs shows significant variability across different runs, across different flow cells, and even across different lanes of the same flow cell. Moreover, detected binding is not the same even when the same lobe interrogates the same SNAP type in the same lane of the flow cell in two different cycles of the same run; and (2) it is impractical to analyze purified or recombinant protein in an isolated lane on the platform for every type of protein of interest.

One important principle behind Adaptive Decode is that the results of previous on-platform experiments provide initial estimates of a binding model matrix. Defining this binding model matrix to understand its role in decoding proteins is beneficial.

The binding model matrix includes a collection of binding models for various SNAP types, where the SNAP types is defined by the protein it carries (or the absence of a protein). Each binding model is a set of predicted binding rates (i.e, frequencies) —one for each lobe in a multi-cycle experiment—of lobes to each SNAP type. The rows of the binding model matrix define the candidate identities of SNAPs. The mixture is composed of the SNAPs included in the binding model matrix.

To characterize proteomic samples, the rows of the binding model matrix would represent every protein that is expected to be present in the sample (e.g. a human proteome for a human proteomic sample). A challenge is generating an accurate binding model for every protein. Even with perfect models for every protein, it may be difficult to distinguish proteins that have similar binding patterns. This problem is more prevalent when trying to distinguish thousands of different proteins. It is expected that errors in the binding models will further confound the ability to accurately characterize highly complex mixtures of proteins.

In Ideal Decode, the binding model matrix is considered to be a fixed quantity that is used as a basis for deconvolving a mixture of proteins. In contrast, Adaptive Decode treats the binding model matrix as an initial estimate of the binding rates that is refined during the course of the method over multiple iterative cycles. We expect these iterations to converge and hope that converged values approach ground truth binding rates.

Assuming that the initial binding model matrix is sufficiently accurate to drive convergence to ground truth, an iterative method in which the initial model is used to make initial inferences about the identities of individual SNAPs on the flow cell. It is expected that many of these initial identifications will be incorrect or uncertain. Even so, these tentative identifications, as if they were correct, are used to update estimates of the binding models. The tentative identifications lead to updated models that are more accurate. These improved models can be used to make a second round of identifications, which would be more accurate than the first. Again, the new set of identifications is used to update the binding models.

If the initial binding model matrix is accurate enough, the binding models for many individual proteins may converge to the true, but unknown, binding rates for those proteins. And at the same time, it is expected that many of the SNAP identifications would be correct and have less uncertainty, leading to an accurate characterization of protein abundances in the sample.

The EM method is designed to solve estimation problems despite "missing data". The missing data is sometimes referred to as the "latent variables". The EM method is well-suited to solving problems where it feels like the estimation problem would be easy to solve if "missing data" was provided and, at the same time, the missing data would be easy to determine if the values of the unknown parameters were known.

At a high level, the EM method feels like a heuristic "trial-and-error" based procedure for solving the two tightly coupled problems above. Its prescription is to make an initial guess at the parameters to estimate. Then, given that guess, calculate what the missing data could look like. Then, use the guess for the missing data to (re-)estimate the parameters. And repeat this cycle.

Providing a bit more detail, the EM method includes multiple iterative cycles, where each cycle has two steps, an expectation step (E-step) and a maximization step (M-step). In the E-step, the current estimate of the parameter values is used to calculate the expected value of the missing data. In the M-step, the expected value of the missing data (along with the observed data), is used to calculate a maximum-likelihood estimate of the parameters. The EM method converges to a solution for many problems.

In general, there are multiple ways to address a given problem using the framework of the EM method. Usually, there are two quantities to determine, and it may not be obvious how to specify which one is the latent variable. Often, the choice becomes clear when one performs the calculations prescribed by the E-step and the M-step. For example, it is often easier to calculate expectations for discrete valued random variables—or even better, binary-valued random variables in the E-step.

Differential calculus is used to find the maximum likelihood estimate for the vector of continuous-valued parameters. In particular, an expression is derived for the (vector) derivative of the likelihood with respect to the parameters of interest and then set the derivative to zero—a necessary condition satisfied at the maximum. The solution of the derivative equation may have a closed-form or may require a numerical solution (e.g. gradient descent).

Representation of Unknown SNAP IDs in Adaptive Decode is a problem in which one can define the missing data as the identities of the SNAPs. At first glance, SNAP identities would seem to be a function mapping each of Q SNAPs to one of the M candidate identities. The assertion that the identity of the $4^{th}$ SNAP is candidate 7 is represented by I(4)=7.

At first glance, this seems acceptable unless the EM method is considered. What would it mean to calculate the expectation of SNAP identities, represented by a function I(q), if we assert that I(4)=7 with probability ½ and I(4)=9 with probability ½. The expectation of I(4) would be 8. This is a nonsensical answer because candidate 8 would be, in general, unrelated to candidates 7 and 9, assuming the candidates can be enumerated.

The solution is to introduce the concept of an identity indicator function. In general, an indicator function is a different way to represent a mapping between two discrete-valued variables as a binary function of two variables. This would represent the assertion that the identity of SNAP 4 is candidate 7 as X(4,7)=1. This represents the probabilistic assertions, as follows:

$$Prob(X(4,7)=1)=\frac{1}{2},\ Prob(X(4,9)=1)=\frac{1}{2},$$

and Prob(X(m, 7)=1)=0 for $m \notin \{7,9\}$.

The EM Method as an Approach to Solve "Missing-Data Problems". "Missing data" can be thought of as information that could be added to the observed data to form an "augmented data set". Given the augmented data set, the estimation problem would be routine. In Adaptive Decode, the missing data is the (true) identity of each SNAP and the observed data are the binding measurements at this SNAP.

In this problem, if we had not only the multi-cycle binding measurements at each SNAP but also the identities of each SNAP—the two together forming an "augmented data set"-then it would be trivial to calculate the binding models for each of M candidates that are represented in the mixture of SNAPs.

One useful example to consider where we do have an augmented data set is the NULL lane of a flow cell. In this case, do we know the ground truth identity of every SNAP? When we do, we calculate the binding model directly and routinely by counting the number of SNAPs where binding is observed and not observed, respectively, i.e. 1's and 0's in each cycle.

In a mixture lane, something similar can be done, given the SNAP identities. For example, first partition the SNAPs by ID and then repeat the calculation above for each partition.

The EM method encourages the performance of something similar. The method suggests an assumption that the SNAP IDs in the lane are known. For example, by replacing the true ID's with a best or optimized guess and combining that with the binding measurements to form an augmented data set. And finally, estimating the binding model matrix for this lane in a way similar to the NULL lane, where both pieces of the puzzle are found, the binding measurements plus an ID for each and every SNAP.

The "best guess" at the SNAP IDs is the output of the E-step in each iteration. The E-step is followed by the M-step. In use of the EM method for Adaptive Decode, the M-step generated an estimate of the binding model matrix using the augmented data set that "Maximization" refers to finding the maximum-likelihood estimate—the vector of parameter values that increases, or even maximizes, the likelihood of the observed data given the expected value of the latent variable. In terms of this problem, the binding model matrix is estimated as the collection of binding model vectors for our M candidates—that maximizes (or increases) the likelihood of the observed data-given the model and a proxy for the SNAP identities.

As mentioned above, the process starts with an initial estimate of the binding model matrix and tries to proceed. In the E-step of the first iteration, a first round of SNAP IDs is made. Those SNAP IDs are made to update the binding model matrix in the M-step of the first iteration. In the second iteration, the initial binding model matrix is replaced with the updated version that was calculated in the M-step of the first iteration to make a second round of SNAP IDs. The first round of SNAP IDs is replaced with the (improved) second round of IDs to update the binding model matrix again in the M-step. This process is repeated until convergence or until reaching a point of diminishing returns where subsequent improvements are so small that they are not worth the computational time to achieve them.

We are now ready to define notation to specify the EM method. We'll use this notation to calculate the E-step and M-step.

- Q: # of SNAPs. All calculations refer to SNAPs on a single lane of flow cell.
- q: SNAP index. $q \in \{1, 2, \ldots Q\}$
- N: # of assay cycles.
  - A binding measurement is attempted at every SNAP in every cycle of the assay.
  - If the same lobe is used in multiple cycles in the assay, an estimate of detected binding rate—an entry in the binding model matrix—is calculated for each cycle, rather than one estimate per lobe.
- n: cycle index $n \in \{1, 2, \ldots N\}$.
- b: binding measurement matrix.
  - b is a Q×N matrix, one row for each SNAP, one column for each assay cycle.
  - We can write b as a column vector composed of Q row vectors $$b = \begin{bmatrix} b_1 \\ b_2 \\ \vdots \\ b_Q \end{bmatrix}$$

- $b_q=[b_{q1}\ b_{q2} \ldots b_{qN}]$, row q of the binding measurement matrix, represents binding measurements across N assay cycles at SNAP q. $b_q$ is used to infer the identity of SNAP q.
  - The value of $b_{qn} \in \{0,1,2\}$ for each $(q,n) \in \{1, 2, \ldots Q\} \times \{1, 2, \ldots N\}$ indicates whether binding was detected in cycle n at SNAP q.
    - $b_{qn}=0$ means "binding was not detected"
    - $b_{qn}=1$ means "binding was detected"
    - $b_{qn}=2$ means "binding status is unknown" because a remove failure was observed in the previous cycle at the same SNAP. Cycles where $b_{qn}=2$ are explicitly excluded from all calculations.
- M: # of candidate identities. A list of candidate identities for the SNAPs on a given flow cell, or perhaps in a single lane of the flow cell is a key input to the method.
  - Each SNAP is assumed to have one of these candidate identities. The identity of each SNAP is unknown but inferred from the binding measurements at that SNAP.
  - When a protein molecule is displayed on the SNAP (as desired), the identity of the SNAP is given by the identity of the protein.
  - If no protein is displayed on the SNAP, the SNAP is identified as "NULL".
  - NULL is always included as one of the candidate identities.
- m: candidate index $m \in \{1, 2, \ldots M\}$
- r: binding model matrix.
  - The binding model matrix is an M×N matrix, representing a collection of binding models for M−1 proteins and NULL. Each binding model is a row in the matrix.

$$r = \begin{bmatrix} r_1 \\ r_2 \\ \vdots \\ r_M \end{bmatrix}$$

- Row vector $r_m=[r_{m1}\ r_{m2} \ldots r_{mN}]$ is the binding model for candidate m. The binding model for candidate m represents a prediction of the fraction of SNAPs of type m where binding would be detected in each of N assay cycles.
    - Roughly speaking, for each $q \in \{1, 2, \ldots Q\}$, SNAP q is "identified"—i.e. its true, unknown identity is inferred—by comparing the observed binding vector $b_q$ to each row of the binding model matrix r.
    - More precisely, we calculate the likelihood of observing $b_q$ given binding model $r_m$, for each candidate identity $m \in \{1, 2, \ldots M\}$.
  - $r_{mn}$ represents a model probability that binding would be detected for a SNAP of identity m in SNAPs in cycle n of the assay given that a successful measurement was obtained.
    - We use the term "probability" and "rate" interchangeably to refer to elements $r_{mn}$ of the binding model matrix r.
    - The underlying "rate" $r_{mn}$ that we are modeling can be thought of as the quantity $$\frac{C_{mn1}}{C_{mn1} + C_{mn0}}$$

- where $C_{mn1}$ and $C_{mn0}$ refer to the numbers of SNAPs of identity m in a given lane of the flow cell where binding is detected or not detected, respectively, not including those SNAPs where the binding status cannot be determined.
    - "Rate" is intended to denote the frequency at which binding outcomes occur in a population of SNAPs, rather than a statement about the time-dependence of binding.
  - The utility of the platform to characterize proteomic samples is based on the assumption that the lobes used across multiple cycles of the assay produce detected binding at different rates for different types of SNAPs.
  - We assume that we have initial estimates of these binding rates for each lobe, SNAP type pair—i.e. a initial estimate of the binding model matrix.
  - The Adaptive Decode method attempts to refine the initial estimate of the binding model matrix to arrive at a highly accurate estimate of the ground-truth matrix.
  - We explicitly assume that binding rates for the same type of SNAP differ in different flow cells and even in different lanes of the same flow cell.

X: identity indicator matrix. The identity indicator matrix is a Q×M matrix, with one row per SNAP and one column per candidate identity. Each SNAP has a (ground-truth) identity, which we assume is one of the M candidates (including NULL as a candidate). We can write X as a column vector of row vectors.

$$X = \begin{bmatrix} X_1 \\ X_2 \\ \vdots \\ X_Q \end{bmatrix}$$

For each q∈{1, 2, . . . Q}, row vector $X_q=[X_{q1}\ X_{q2}\ \ldots\ X_{qM}]$ represents the ground-truth identity of SNAP q.

Exactly one element in each row has a value of one and the other elements have a value of zero.

For example, if SNAP q has identity m, then $X_{qm}=1$ and for m'≠m $X_{qm}=0$.

In both Adaptive Decode and in Iterative Ideal Decode, X represents the latent variable, whose expectation is calculated in the E-step. The term "latent variable" refers to missing data.

π: prior probability vector. The prior probability vector $\pi=[\pi_1\ \pi_2\ \ldots\ \pi_M]$ is a row vector of M values, one for each candidate.

The value $\pi_m$ represents the probability we would assign to candidate M for each SNAP in a flow-cell lane, i.e. independent of or "prior to" considering binding measurements acquired a single SNAP.

The prior also represents the (unknown) abundances of different types of SNAPs in the prep that was deposited in a given flow cell lane.

A uniform prior $$\pi = \frac{1}{M}[1\ 1\ \ldots\ 1]$$

reflects an absence of prior information, and this is a typical choice in many problems.

In Iterative Ideal Decode, we use a uniform prior as an initial estimate and iteratively update the prior based upon inferred SNAP identifications across the entire population.

p: data likelihood matrix. The data likelihood matrix vector is a Q×M matrix, with one row per SNAP and one column per candidate identity. It has the same form as the identity indicator matrix.

Like the identity indicator matrix, it can be written as a column vector of Q row vectors.

$$p = \begin{bmatrix} p_1 \\ p_2 \\ \vdots \\ p_Q \end{bmatrix}$$

For each q∈{1, 2, . . . Q}, the row vector $p_Q=[p_{q1}\ p_{q2}\ \ldots\ p_{qM}]$ represents a collection of data likelihood values for the binding measurement vector $b_q$ observed at SNAP q.

For each candidate identity m∈{1, 2, . . . M}, the entry $p_{qm}$ in the data likelihood matrix indicates the likelihood that measurement vector $b_q$ would be generated by a random-process model for measurements that we expect to obtain from a SNAP of identity m. That random-process model is parameterized by the binding model for candidate m—the row vector $r_m$ of the binding model matrix r.

The data likelihood matrix is important for the inference process as it connects the binding measurements observed at SNAPs, the candidate identities of these SNAPs, and models for detected binding for each candidate.

P: posterior matrix. The posterior matrix has the same form as the posterior matrix a Q×M matrix, with one row per SNAP and one column per candidate identity.

$$P = \begin{bmatrix} P_1 \\ P_2 \\ \vdots \\ P_Q \end{bmatrix}$$

For each q∈{1, 2, . . . Q}, the row vector $P_q=[P_{q1}\ P_{q2}\ \ldots\ P_{qM}]$ represents a collection of posterior probabilities for the candidate identities given the binding measurement vector $b_q$ observed at SNAP q.

We use Bayes' Law to calculate the posterior probability from the prior vector and the data likelihood matrix.

For each candidate identity m∈{1, 2, . . . M}, the entry $P_{qm}$ in the posterior probability matrix indicates the probability that the identity of SNAP q is candidate m.

Ideally, and desirably, each calculated value of the posterior probability matrix $P_{qm}$ would be very close to the corresponding value in the identity indicator matrix $X_{qm}$.

We have now introduced the quantities necessary to derive formulas for (1) E-step: The expectation of the latent variable (SNAP IDs), and (2) M-step: The maximum-likelihood parameter estimate (binding model matrix).

Regarding Data Likelihood, in the on-platform assay, for each SNAP in a flow cell lane, i.e. q∈{1, 2, . . . Q}, we perform N binding measurements, one for each cycle n∈{1, 2, . . . N}. We can organize these measurements to form a row vector $b_q=[b_{q1}\ b_{q2}\ \ldots\ b_{qN}]$ at SNAP q. We could also organize the entire set of measurements over all SNAPs in the lane by stacking each of the Q row vectors to form a large matrix we call the binding measurement matrix b. However, in the conventional practice of Decode, we focus our attention on individual SNAPs.

For each SNAP q∈{1, 2, . . . Q}, and for each candidate m∈{1, 2, . . . M}, we calculate a data likelihood value for the pair (q, m). The calculated value $p_{qm}$ represents the (model) likelihood that the vector of binding measurements observed at SNAP q—namely $b_q$—would be produced by a SNAP of identity m.

The formula we use for calculating the data likelihood value at single SNAP is:

$$p_{qm} = \left(\prod_{b_{qn}=1} r_{mn}\right)\cdot\left(\prod_{b_{qn}=0} 1 - r_{mn}\right)$$

The product above has two factors. Both products are calculated over cycles (values of n), with two distinct subsets of cycles appearing in the two products. The first factor is the product of probabilities that binding would be detected in those cycles where binding was detected at SNAP q ($b_{qn}$=1). The second factor is the product of probabilities that binding would not be detected in those cycles where a binding event was not detected at SNAP q ($b_{qn}$=0).

The probability of detecting binding in cycle n for a SNAP of candidate identity m is given by $r_{mn}$, an entry in the binding model matrix r. The probability of not detecting binding in the same cycle n for the same candidate identity m is $1-r_{mn}$. Notice that any cycles where a "2" was recorded (i.e. $b_{qn}$=2), representing an unknown outcome, do not contribute to the data likelihood.

Regarding the Posterior Probability Matrix, a posterior probability matrix using methods for a non-uniform prior is also calculated. In general, each entry $P_{qm}$ of the posterior matrix is calculated from the prior vector and the data likelihood matrix as follows:

$$P_{qm} = \frac{\pi_m \cdot p_{qm}}{\sum_{m=1}^{M} \pi_m \cdot p_{qm}}$$

For the special case of the uniform prior, the factor $\pi_m$ does not dependent on the candidate index and can be pulled out of the sum in the denominator and used to cancel the same factor that occurs in the numerator.

$$P_{qm} = \frac{\frac{1}{M} \cdot p_{qm}}{\sum_{m=1}^{M} \frac{1}{M} \cdot p_{qm}} = \frac{\frac{1}{M} \cdot p_{qm}}{\frac{1}{M} \cdot \sum_{m=1}^{M} p_{qm}} = \frac{p_{qm}}{\sum_{m=1}^{M} p_{qm}}$$

Like the identity indicator matrix, each row of the posterior matrix sums to one.

$$\sum_{m=1}^{M} P_{qm} = \sum_{m=1}^{M} X_{qm} = 1$$

Our aspiration is that the entries of the posterior matrix would equal the identity indicator matrix, indicating correct identification of each SNAP with no uncertainty.

Regarding the E-step for calculation of the Expectation of the Latent Variable (Identity Indicator Matrix), we use the current estimate of the binding model matrix r to calculate the expected value of the identity indicator matrix. In the first iteration, the current estimate of the binding model matrix is the initial estimate, provided as input to the method. In subsequent iterations, it is the output of the M-step from the previous iteration. The expected value of a matrix is the expected value of each of its scalar-valued entries.

In the first iteration of the EM method, the current estimate of the binding model matrix is the initial estimate. Therefore, a set of binding models for each of the M candidates (including NULL) is a vital input to the method, along with the observed binding measurements in a flow-cell lane. The initial binding model may come from: (1) binding measurements of SNAPs in another lane of the same flow cell or a different flow cell, (2) off-platform measurements of binding, (3) a measured or theoretical tertiary structure of a protein, (4) de novo calculations originating from a protein's primary sequence, or (5) any combinations thereof.

Given the current estimate of the binding model, we calculate the entries in the posterior probability matrix as described above, with intermediate steps of calculating the prior vector and the data likelihood matrix.

After we have the posterior probability matrix, we calculate the expectation of the latent variable—the identity indicator matrix X.

We now define a "pseudocount" matrix x, which is defined as the expectation of the identity indicator matrix X.

$$x = \langle X \rangle$$

$$\begin{bmatrix} x_{11} & x_{12} & \dots & x_{1M} \\ x_{21} & x_{22} & \dots & x_{2M} \\ \vdots & \vdots & \ddots & \vdots \\ x_{Q1} & x_{Q2} & \dots & x_{QM} \end{bmatrix} = \begin{bmatrix} \langle X_{11} \rangle & \langle X_{12} \rangle & \dots & \langle X_{1M} \rangle \\ \langle X_{21} \rangle & \langle X_{22} \rangle & \dots & \langle X_{2M} \rangle \\ \vdots & \vdots & \ddots & \vdots \\ \langle X_{Q1} \rangle & \langle X_{Q2} \rangle & \dots & \langle X_{QM} \rangle \end{bmatrix}$$

In contrast to the way we defined the identity indicator matrix earlier in this document, i.e. having deterministic but unknown values, here we reflect our uncertainty about those deterministic values by modeling $X_{qm}$ as a binary random variable, whose outcomes 1 and 0, have probabilities given by $P_{qm}$ and $1-P_{qm}$, respectively, where $P_{qm}$ is the corresponding value in the posterior probability matrix, i.e. at SNAP q for candidate m. Each entry $x_{qm}$ in the pseudocount matrix is the expectation of the binary-valued random variable $X_{qm}$ for each $q \in \{1, 2, \dots, Q\}$ and $m \in \{1, 2, \dots, M\}$.

The expectation of a binary random variable is simply the probability of that its value is 1.

$$x_{qm} = \langle X_{qm} \rangle = 1 \cdot P_{qm} + 0 \cdot (1 - P_{qm}) = P_{qm}$$

The three quantities that appear in the equation above X, P, and x are intimately related. A row of the pseudocount matrix x can be interpreted as partitioning each (unit) SNAP among the M candidates, providing each candidate a fractional number of SNAPs or "pseudocounts". The pseudocounts $x_q=[x_{q1}, x_{q2}, \dots x_{qM}]$ assigned to each candidate at SNAP q is equal to the respective posterior probabilities $P_q=[P_{q1}, P_{q2}, \dots P_{qM}]$, i.e. row q in the posterior probability matrix.

The expected value of any discrete-valued random variable is a sum which one term for each possible outcome of the random variable. For a continuous-valued random variable, the sum is replaced by an integral. For a binary-valued random variable, there are two terms in the sum, corresponding to the two values 0 and 1. Each term is the product of an outcome value times the probability of that outcome value. The expectation can be thought of as the probability-weighted sum of outcome values. For a binary random variable, one term (the first term below) evaluates to the posterior probability pam and the second term evaluates to zero.

$$\langle X_{qm} \rangle = 1 \cdot P_{qm} + 0 \cdot (1 - P_{qm}) = P_{qm}$$

Because the entries of $X_{qm}$ are binary-valued, i.e. $X_{qm} \in \{0,1\}$, $x_{qm}$—the expected value of $X_{qm}$—is numerically equivalent to the corresponding entry in the posterior matrix $P_{qm}$. This is a fortunate coincidence that arises from representing the "missing data" in our problem in terms of binary-valued quantities. Although they are numerically equivalent, the posterior matrix P and the pseudocount matrix x are distinct quantities that should not be confused.

Ideally, at each SNAP, we would assign one (pseudo) count to the candidate representing the SNAP's (true) identity and no counts to the other candidates. This is the result of a "winner-take-all" approach, in which one count is assigned (correctly or incorrectly) to the candidate with the highest (model) posterior probability. An alternative to "winner-take-all" is assigning an identity (count) to a SNAP only when the posterior probability of the "winner" exceeds a pre-defined threshold value. If the winner fails to exceed the threshold, no call is made for this SNAP, as the binding measurement vector is judged to be ambiguous.

We also calculate the (posterior) probability for each candidate at each SNAP in the E-step of the EM method. However, a difference from the "winner-take-all" method is a pseudocount method. The posterior probability in the EM method is used to partition each SNAP into M "SNAPlets", each with a fractional number of pseudocounts based upon the expected values of the entries in the identity indicator matrix, which in turn, are numerically equivalent to the values of the posterior probabilities.

Regarding the M-step and the Maximum-Likelihood Estimate of the Parameter (Binding Model Matrix), the result of the M-step (maximization) is to produce a maximum-likelihood estimate of the target parameter given the expected value of the latent parameter. In the specific context of Adaptive Decode, we are determining values in the binding model matrix r that maximize the likelihood of observing the values in the binding measurement matrix given our current identifications of individual SNAPs. These "identifications" are represented by the output of the E-step—a set of expected values for the entries in the identity indicator matrix. We view these values as describing pseudocounts of SNAPs, with defined identities and observed measurements.

In general, a maximum-likelihood estimate is obtained by expressing the data likelihood for the observed binding measurement matrix (represented by measured values) in terms of the SNAP pseudocounts (represented by estimated values) as a function of the binding model matrix (represented as an algebraic variable). Then, the derivative of the data likelihood with respect to the binding model matrix entries is evaluated and expressed as a function of the binding model matrix (still represented as an algebraic variable). Finally, the estimate is produced by finding the values for the binding model matrix for which the derivative is equal to zero. In this case, the matrix equation represents Mx N scalar equations, which must be solved simultaneously.

In general, the solution of the derivative equation does not have a closed form and may be a non-linear function of multiple variables. The implementation of the M-step may be complicated, involving gradient descent or random sampling methods. We are very fortunate that the equations for the Mx N model binding values are completely decoupled; that each equation is linear in a single parameter; and that a simple closed-form solution is available and easily computed.

Even so, the derivative calculation is not straightforward. We can gain some insights about the problem by considering some special cases and working through some simple related problems.

A related issue is the Maximum-Likelihood Estimation of the Binding Model for the Null Lane. The first insight is that we already have a method for calculating a binding model for NULL SNAPs. We calculate the binding model trivially for NULL SNAPs because this is a situation where we know the ground-truth identity of every SNAP. In the NULL lane of the flow cell, we deposit NULL SNAPs; there's no protein in the NULL lane. In contrast, in lanes that are (nominally) composed of a purified protein, we, in fact, deposit a mixture of two species of SNAPs: SNAPs carrying the protein and also NULL SNAPs (carrying no protein). As a result, the only situation where we can establish the ground-truth identity of each SNAP is in the NULL lane of a flow cell.

For the NULL lane of the flow cell, our method for calculating the binding rate in each of N cycles is to count the number of SNAPs where we see 1's and 0's in that cycle. Suppose that in cycle n, the counts of 1's and 0's are $C_{n1}$ and $C_{n0}$ respectively. We calculate the binding rate for NULL SNAPs in cycle n as follows:

$$r_n = \frac{C_{n1}}{C_{n1} + C_{n0}}$$

As mentioned before, when we make the estimate of the binding rate, we exclude SNAPs with values of 2. If we repeat this procedure for each cycle, $n \in \{1, 2, \ldots N\}$, we produce a binding rate estimate for each cycle. We combine these to form a binding model for NULL $$r = [r_1 \ r_2 \ \ldots \ r_N]$$

We can place this vector as a row in the binding model matrix, which in general has M such rows, associated with the binding models for M candidates. In other words, these estimates provide one row in the model matrix, because NULL is always one of the M candidates we consider when identifying SNAPs.

A question is whether the method of estimating the binding rate for NULL SNAPs in cycle n is merely a heuristic method or whether it truly provides a maximum-likelihood estimate. Frequently, carrying out the calculations for the maximum-likelihood estimate leads to the satisfying result that our intuition was right: that the intuitive, simple calculation is in fact the maximum-likelihood estimate as well. Sometimes, the maximum-likelihood estimate is quite similar but not the same, indicating that our intuition was only approximately correct and that we can produce a more accurate result by choosing the maximum-likelihood formula. In other cases, the maximum-likelihood estimate is so onerous to compute that we may decide that the simple heuristic calculation is "good enough" for our purposes.

Now, we will verify that the simple formula above is indeed the maximum-likelihood estimate for the NULL binding model. We start with the expression for the (per-SNAP) data-likelihood described above and copied here.

$$p_{qm} = \left(\prod_{b_{qn}=1} r_{mn}\right) \cdot \left(\prod_{b_{qn}=0} 1 - r_{mn}\right)$$

This is the (model) likelihood of observing the sequence of binding measurements $b_q=[b_{q1}\ b_{q2} \ldots b_{qN}]$ at SNAP q when the SNAP's identity is candidate m whose binding rates are given by the vector $r_m=[r_{m1}\ r_{m2} \ldots r_{mN}]$.

We assume that the binding measurements across all Q SNAPs on the flow cell are independent and identically distributed. The assumption that they are identically distributed is not true, in general. But in this case, we are considering a uniform population of NULL SNAPs. We will seek to use the assumption that SNAPs are identically distributed during our derivation of the M-step. But we can only do so, in general, if we are considering a subset of SNAPs that have the same identity.

In this case, we assume that candidate m denotes NULL and that all SNAPs have identity m (NULL). Now, we compute the likelihood of the entire matrix of binding measurements. According to our IID assumption, the likelihood is the product of per-SNAP likelihoods.

$$L = \prod_{q=1}^{Q} p_{qm} = \prod_{q=1}^{Q}\left[\left(\prod_{b_{qn}=1} r_{mn}\right)\cdot\left(\prod_{b_{qn}=0} 1 - r_{mn}\right)\right]$$

The next step is to take the derivative dL/dr of scalar-valued L with respect to matrix r. The result is a matrix of scalar-valued derivatives, one entry in dL/dr for each entry in L.

$$r = \begin{bmatrix} r_1 \\ r_2 \\ \vdots \\ r_M \end{bmatrix} = \begin{bmatrix} r_{11} & r_{12} & \cdots & r_{1N} \\ r_{21} & r_{22} & \cdots & r_{2N} \\ \vdots & \vdots & \ddots & \vdots \\ r_{M1} & r_{M2} & \cdots & r_{MN} \end{bmatrix}$$

$$\frac{dL}{dr} = \begin{bmatrix} \frac{dL}{dr_{11}} & \frac{dL}{dr_{12}} & \cdots & \frac{dL}{dr_{1N}} \\ \frac{dL}{dr_{21}} & \frac{dL}{dr_{21}} & \cdots & \frac{dL}{dr_{2N}} \\ \vdots & \vdots & \ddots & \vdots \\ \frac{dL}{dr_{M1}} & \frac{dL}{dr_{M2}} & \cdots & \frac{dL}{dr_{MN}} \end{bmatrix}$$

We need to be careful not to confuse the indices for cycles in the likelihood formula with indices in our derivative matrix. In this case, we are considering only SNAPs of candidate m, so m is fixed. However, we must rewrite the likelihood equation in terms of cycle indices n' to distinguish from the cycle n we are selecting for the derivative calculation.

$$L = \prod_{q=1}^{Q} p_{qm} = \prod_{q=1}^{Q}\left[\left(\prod_{b_{qn'}=1} r_{mn'}\right)\cdot\left(\prod_{b_{qn'}=0} 1 - r_{mn'}\right)\right]$$

Now, we take the derivative of both sides of the equation.

$$\frac{dL}{dr_{mn}} = \frac{d}{dr_{mn}}\left[\prod_{q=1}^{Q} p_{qm}\right]$$

And then we calculate the derivative of the total (i.e. all-SNAPs) likelihood in terms of the per-SNAP likelihood.

$$\frac{dL}{dr_{mn}} = \frac{d}{dr_{mn}}\left[\prod_{q=1}^{Q} p_{qm}\right] = L\cdot\sum_{q=1}^{Q}\frac{dp_{qm}}{dr_{mn}}\cdot\left(\frac{1}{p_{qm}}\right)$$

The per-SNAP likelihood is computed similarly.

$$\frac{dp_{qm}}{dr_{mn}} = \frac{d}{dr_{mn}}\left[\left(\prod_{b_{qn'}=1} r_{mn'}\right)\cdot\left(\prod_{b_{qn'}=0} 1 - r_{mn'}\right)\right]$$

$$\frac{dp_{qm}}{dr_{mn}} = p_{qm}\cdot\left[\sum_{b_{qn'}=1}\frac{dr_{mn'}}{dr_{mn}}\cdot\left(\frac{1}{r_{mn'}}\right) + \sum_{b_{qn'}=0}\left(-\frac{dr_{mn'}}{dr_{mn}}\right)\cdot\left(\frac{1}{1 - r_{mn'}}\right)\right]$$

The expression in brackets above has two sums. Together, these sums contain N terms, one for each cycle. It's important to note that only one of these terms is non-zero. For n' ne n, $$\frac{dr_{mn'}}{dr_{mn}} = 0.$$

For n'=n, $$\frac{dr_{mn'}}{dr_{mn}} = \frac{dr_{mn}}{dr_{mn}} = 1.$$

Therefore, our expression simplifies significantly.

$$\frac{dp_{qm}}{dr_{mn}} = \begin{cases} \frac{p_{qm}}{r_{mn}} & \text{if } b_{qn} = 1 \\ -\frac{p_{qm}}{1 - r_{mn}} & \text{if } b_{qn} = 0 \end{cases}$$

We have two possible values for the per-SNAP derivative, depending on whether binding is detected in cycle n for that SNAP, i.e. SNAP q. For example, consider two SNAPs with measured binding vectors [1 1 1] and [0 1 0] where the binding model is [r_1 r_2 r_3].

The per-SNAP likelihood for the first SNAP is $p_1=r_1\cdot r_2\cdot r_3$.

The per-SNAP likelihood for the second SNAP is $p_2=(1-r_1)\cdot r_2\cdot(1-r_3)$ The derivatives of $p_1$ and $p_2$ with respect to $r_1$ show differences that reflect the general equation above.

$$\frac{dp_1}{dr_1} = \frac{d}{dr_1}(r_1\cdot r_2\cdot r_3) = r_2\cdot r_3 = \frac{p_1}{r_1}$$

$$\frac{dp_2}{dr_1} = \frac{d}{dr_1}((1 - r_1)\cdot r_2\cdot(1 - r_3)) = -r_2\cdot(1 - r_3) = -\frac{p_2}{1 - r_1}$$

Now, we combine our expressions for the all-SNAPs derivative and the per-SNAP derivative to arrive at the following equation:

$$\frac{dL}{dr_{mn}} = L\cdot\sum_{q=1}^{Q}\frac{dp_{qm}}{dr_{mn}}\cdot\left(\frac{1}{p_{qm}}\right)$$

$$\frac{dp_{qm}}{dr_{mn}} = \begin{cases} \frac{p_{qm}}{r_{mn}} & \text{if } b_{qn} = 1 \\ -\frac{p_{qm}}{1 - r_{mn}} & \text{if } b_{qn} = 0 \end{cases}$$

$$\frac{dL}{dr_{mn}} = L\cdot\left[\sum_{b_{qn}=1}\frac{p_{qm}}{r_{mn}}\cdot\left(\frac{1}{p_{qm}}\right) - \sum_{b_{qn}=0}\frac{p_{qm}}{1 - r_{mn}}\cdot\left(\frac{1}{p_{qm}}\right)\right]$$

Note that each sum is a sum over SNAPs rather than a sum over cycles. We are considering one cycle n as indicated on the left side of the equation and a situation in which all SNAPs have the same identity, indicated by the index m on the left side of the equation.

In the equation above, factors of $p_{qm}$ cancel out from the numerator and denominator of each sum. Factors dependent on the binding model $r_{mn}$ can be pulled out of the sum because they are the same for all SNAPs—i.e. all SNAPs with the same identity.

$$\frac{dL}{dr_{mn}} = L \cdot \left[\frac{1}{r_{mn}}\left(\sum_{b_{qn}=1} 1\right) - \frac{1}{1-r_{mn}}\left(\sum_{b_{qn}=0} 1\right)\right]$$

The two sums are counts of how many SNAPs have a measured values of 1 and 0 respectively in cycle n. Previously, we defined these quantities as $C_{mn1}$ and $C_{mn0}$ respectively.

$$\frac{dL}{dr_{mn}} = L \cdot \left[\frac{C_{mn1}}{r_{mn}} - \frac{C_{mn0}}{1-r_{mn}}\right]$$

The maximum likelihood estimate $\hat{r}_{mn}$ is determined by setting the right-hand side of the equation above to zero and solving for $r_{mn}$.

$$\frac{dL}{dr_{mn}} = 0 \Rightarrow L = 0 \text{ or } \frac{C_{mn1}}{r_{mn}} - \frac{C_{mn0}}{1-r_{mn}} = 0$$

Because likelihood L>0, we have $$\frac{C_{mn1}}{\hat{r}_{mn}} = \frac{C_{mn0}}{1-\hat{r}_{mn}}$$

Solving for $\hat{r}_{mn}$, we have the desired result.

$$\hat{r}_{mn} = \frac{C_{mn1}}{C_{mn1} + C_{mn0}}$$

The equation is true for all cycles n in {1,2, N}, which allows us to estimate the binding model, a vector of N values, for the NULL model.

This is the "desired" result because it shows that our intuition was correct and that an equation that is simple to understand, to implement, and to calculate provides the estimate of the binding model parameter.

Regarding finding the Maximum-Likelihood Estimate of the Binding Model Matrix in mixtures, in the framework of the M-step of the EM method, the result above can be used to update M binding models in a mixture rather than merely for uniform or homogenous mixtures.

One insight that allows us to extend the result from a homogeneous population to the general case of a mixture is the correct interpretation of the pseudocounts that are produced by the E-step of the method.

A correct way to interpret pseudocounts is that we transform each SNAP into M "SNAPlets", each with a fractional abundance. The binding measurements associated with each SNAPlet is the same as were associated with the original SNAP from which the SNAPlets were derived. Working backwards from the solution, we want to arrive at an equation related to the previous result.

$$\hat{r}_{mn} = \frac{C_{mn1}}{C_{mn1} + C_{mn0}}$$

Is it correct to reinterpret the counts $C_{mn1}$ and $C_{mn0}$ as the sums of fractional pseudocounts for subsets of SNAPlets with the same identity? In this case, our formulas would change as follows $$C_{mn1} = \sum_{b_{qn}=1} 1 \rightarrow C_{mn1} = \sum_{b_{qn}=1} x_{qm}$$

$$C_{mn0} = \sum_{b_{qn}=1} 1 \rightarrow C_{mn0} = \sum_{b_{qn}=0} x_{qm}$$

We can also write the equations on the left in terms of the identity indicator matrix. In a homogeneous population of SNAPs of identity m, X_qm=1. So, we have the result that the EM method seems to prescribe that we replace the identity indicator matrix, which represents the ground-truth identity of each SNAP, with its expected value, the pseudocount matrix calculated in the E-step.

$$C_{mn1} = \sum_{b_{qn}=1} X_{qm} \rightarrow C_{mn1} = \sum_{b_{qn}=1} x_{qm}$$

$$C_{mn0} = \sum_{b_{qn}=1} X_{qm} \rightarrow C_{mn0} = \sum_{b_{qn}=0} x_{qm}$$

In the case of a mixture, we would partition the SNAPlets into M groups, one for each candidate. The reason we can do this is that each SNAPlet has a defined identity, albeit with a fractional count, rather than an indeterminate identity represented by posterior probabilities.

Thinking one step further upstream in the calculation, we consider the form of the all-SNAP (lets) likelihood function that would give rise to the desired result. Previously, we had the all-SNAPs likelihood function $$L = \prod_{q=1}^{Q} p_{qm}$$

Suppose we were to replace each SNAP that had one count and determinate identity m with M SNAPlets that have M different determinate identities (one for each candidate) fractional counts x_m=. . .

$$L = \prod_{q=1}^{Q}\prod_{m=1}^{M} (p_{qm})^{x_{qm}}$$

Introducing the pseudocounts as exponents in the likelihood equation provides a solution. This makes sense if we think about how we would rewrite the likelihood expression in the case where the same binding vector of binding measurements occurred x times for SNAPs with identity m. We would have x identical factors of $p_{qm}$ in the likelihood expression. And if we chose to do so, we could express the likelihood as a product over distinct values of $b_q$. In that case $p_{qm}$ would be raised to the x power.

Therefore, we conclude that this, indeed, is the correct way to account for the pseudocounts produced in the E-step. Now, we calculate the derivative with respect to $r_{mn}$ as before, taking care to label the candidate index for the various SNAPlets associated with SNAP q as m' to distinguish them from the fixed value of m on the left-hand side that indicates the candidate model for which we are calculating the derivative.

$$\frac{dL}{dr_{mn}} = \frac{d}{dr_{mn}}\left(\prod_{q=1}^{Q}\prod_{m'=1}^{M}(p_{qm'})^{x_{qm'}}\right)$$

Using the same result as before, but now considering the product of Q. M factors.

$$\frac{dL}{dr_{mn}} = \frac{d}{dr_{mn}}\left(\prod_{q=1}^{Q}\prod_{m'=1}^{M}(p_{qm'})^{x_{qm'}}\right) = L\cdot\sum_{q=1}^{Q}\sum_{m'=1}^{M}\frac{d}{dr_{mn}}\left((p_{qm'})^{x_{qm'}}\right)\cdot\left(\frac{1}{(p_{qm'})^{x_{qm'}}}\right)$$

We use the chain rule to evaluate the derivative $$\frac{d}{dr_{mn}}\left((p_{qm'})^{x_{qm'}}\right) = \begin{cases} x_{qm}\cdot(p_{qm})^{x_{qm}-1}\cdot\frac{dp_{qm}}{dr_{mn}} & \text{if } m' = m \\ 0 & \text{if } m' \neq m \end{cases}$$

Combining the equations above, we have $$\frac{dL}{dr_{mn}} = L\cdot\sum_{q=1}^{Q}x_{qm}\cdot(p_{qm})^{x_{qm}-1}\cdot(p_{qm})^{-x_{qm}}\cdot\frac{dp_{qm}}{dr_{mn}}$$

Using another result from before $$\frac{dp_{qm}}{dr_{mn}} = \frac{dp_{qm}}{dr_{mn}} = \begin{cases} \frac{p_{qm}}{r_{mn}} & \text{if } b_{qn} = 1 \\ -\frac{p_{qm}}{1-r_{mn}} & \text{if } b_{qn} = 0 \end{cases}$$

And combining equations $$\frac{dL}{dr_{mn}} = L\cdot\left[\sum_{b_{qn}=1}x_{qm}\cdot(p_{qm})^{x_{qm}-1}\cdot(p_{qm})^{-x_{qm}}\cdot\frac{p_{qm}}{r_{mn}} - \sum_{b_{qn}=0}x_{qm}\cdot(p_{qm})^{x_{qm}-1}\cdot(p_{qm})^{-x_{qm}}\cdot\frac{p_{qm}}{1-r_{mn}}\right]$$

As before, factors of $p_{qm}$ cancel out from both factors and we pull out a factor independent of q from each sum.

$$\frac{dL}{dr_{mn}} = L\cdot\left[\frac{1}{r_{mn}}\sum_{b_{qn}=1}x_{qm} - \frac{1}{1-r_{mn}}\sum_{b_{qn}=0}x_{qm}\right]$$

We now replace sums over pseudocounts with $C_{mn1}$ and $C_{mn0}$.

$$\frac{dL}{dr_{mn}} = L\cdot\left[\frac{C_{mn1}}{r_{mn}} - \frac{C_{mn0}}{1-r_{mn}}\right]$$

We arrive at the same equation for our estimate, except that we interpret these counts as pseudocount sums rather than SNAP counts.

$$\hat{r}_{mn} = \frac{C_{mn1}}{C_{mn1}+C_{mn0}}$$

One implementation of the adaptive decode method is to first construct an initial estimate for the binding model matrix r (Mx N) including a row for the binding model for NULL SNAPs. Second, for each m∈{1, 2, . . . M}, set $$\pi_m = \frac{1}{M}.$$

Third, E-step:

a. For each q∈{1, 2, . . . Q} and each m∈{1, 2, . . . M}, set $$p_{qm} = \left(\prod_{b_{qn}=1} r_{mn}\right)\cdot\left(\prod_{b_{qn}=0} 1-r_{mn}\right)$$

b. For each q∈{1, 2, . . . Q} and each m∈{1, 2, . . . M}, set $$x_{qm} = \frac{\pi_m\cdot p_{qm}}{\sum_{m=1}^{M}\pi_m\cdot p_{qm}}.$$

Fourth, M-step: For each m∈{1, 2, . . . M} and each n∈{1, 2, . . . N}, set c. $C_{mn1} = \sum_{b_{qn}=1} x_{qm}$ d. $C_{mn0} = \sum_{b_{qn}=0} x_{qm}$ e. $\hat{r}_{mn} = \frac{c_{mn1}}{c_{mn1}+c_{mn0}}$ Fifth, Repeat steps 3 and 4 iteratively. Report binding model matrix r. Sixth, for each m∈{1, 2, . . . M}, determine $$C_m = \Sigma_{q=1}^{Q}x_{qm}.$$

Seventh, Determine $$C=\Sigma_{m=1}^{M}C_m.$$

Eighth, for each m∈{1, 2, . . . M}, determine $\pi_m=C_m/C$. Ninth, Report estimated abundances π.

Regarding use of beta-distributed priors to restrain updated probe probability binding model, because the beta distribution is the conjugate prior for the Bernoulli data likelihood on observed binding measurements, replacing the Gaussian prior on binding rates with a beta prior leads to a closed-form solution for the binding rates in the M-step of the EM algorithm, accelerating convergence. The alpha and beta parameters of the beta distribution can be viewed as pseudocounts for positive and negative measurements, respectively of lobe binding to proteins or proteoforms.

Regarding proteoforms, in a first step, parallel instances of the EM algorithm (one for each probe-epitope pair) are used to estimate the on-target and off-target binding rates for each probe-epitope pair. In a second step, a modified implementation of the EM algorithm is used to estimate proteoform abundances, locking the binding rates established in the first step. The two-step method leads to faster and more robust estimates in proteoform analysis.

What is claimed is:

1. A system for characterizing proteins from a sample, comprising:

a substrate having proteins deposited thereon, each protein of the proteins attached to unique spatial addresses on the substrate;

a fluidic system configured to expose the proteins attached to the unique spatial addresses on the substrate to a series of affinity reagents;

a detector configured to determine an observed binding measurements model indicating positive binding measurement outcomes and negative binding measurement outcomes for the proteins binding to the series of affinity reagents; and a computing device comprising one or more computer processors, configured to:

receive a first probe probability binding model indicating estimated probabilities of the series of affinity reagents binding to one or more candidate proteins that may be in the sample;

assign, to each candidate protein, a pseudocount for each protein of the proteins, wherein the pseudocount is a value proportional to the calculated probability for the protein being identified as the candidate protein, the pseudocounts calculated based on (i) the observed binding measurements model and (ii) the first probe probability binding model; and quantify the proteins by summing, for each of the candidate proteins, the pseudocounts across all the proteins to determine a first abundance for each of the candidate proteins.

2. The system of claim 1, the computing device further configured to:

determine a second probe probability binding model based on the pseudocounts and the observed binding measurements model.

3. The system of claim 2, the computing device further configured to:

assign, to each candidate protein, an updated pseudocount for each protein of the proteins, wherein the updated pseudocount is a value proportional to the calculated probability for the protein being identified as the candidate protein, the updated pseudocounts based on (i) the observed binding measurements model, (ii) the second probe probability binding model, and (iii) the first abundance for each of the candidate proteins; and quantify the proteins by summing the updated pseudocounts across all the proteins to determine a second abundance for each protein of the candidate proteins, the first abundances and the second abundances being different.

4. The system of claim 1, the computing device further configured to:

receive initial estimated abundance information of the candidate proteins for the proteins of the sample, and wherein calculating the pseudocounts is further based on the initial estimated abundance information.

5. The system of claim 4, wherein the initial estimated abundance information is different than the first abundance information.

6. The system of claim 4, wherein the initial estimated abundance information indicates a uniform distribution of candidate proteins.

7. The system of claim 1, wherein the candidate proteins are proteoforms of a protein species.

8. A method for characterizing proteins using the system of claim 1, comprising:

activating the fluidic system to expose the proteins attached to the unique spatial addresses on the substrate to the series of affinity reagents;

determining the observed binding measurements model from the detector indicating positive binding measurement outcomes and negative binding measurement outcomes for the proteins binding to the series of affinity reagents;

receiving from the computing device the first probe probability binding model indicating estimated probabilities of the series of affinity reagents binding to the candidate proteins that may be in the sample;

assigning, to each candidate protein of the candidate proteins, the pseudocount for each protein of the proteins, wherein the pseudocount is a value proportional to the calculated probability for each protein being identified as the candidate protein, the pseudocounts calculated based on (i) the observed binding measurements model and (ii) the first probe probability binding model; and quantifying the proteins by summing, for each of the candidate proteins, the pseudocounts across all the proteins to determine the first abundance for each of the candidate proteins.

9. The method of claim 8, further comprising:

determining a second probe probability binding model based on the pseudocounts and the observed binding measurements model.

10. The method of claim 9, further comprising:

assigning, to each candidate protein, updated pseudocounts for each protein of the proteins, wherein the updated pseudocount is a value proportional to the calculated probability for the protein being identified as the candidate protein, the updated pseudocounts based on (i) the observed binding measurements model, (ii) the second probe probability model, and (iii) the first abundances for each of the candidate proteins; and quantifying the proteins by summing the pseudocounts across all the proteins to determine second abundances for each of the candidate proteins, the first abundances and the second abundances being different.

11. The method of claim 8, further comprising:

receiving initial estimated abundance information of the candidate proteins for the proteins of the sample, and wherein calculating the pseudocounts is further based on the initial estimated abundance information.

12. The method of claim 11, wherein the initial estimated abundance information is different than the first abundance information.

13. The method of claim 11, wherein the initial estimated abundance information indicates a uniform distribution of candidate proteins.

14. The method of claim 8, wherein the candidate proteins are proteoforms of a protein species.

* * * * *